(12) United States Patent
Viola

(10) Patent No.: US 9,113,872 B2
(45) Date of Patent: Aug. 25, 2015

(54) SURGICAL STAPLING APPARATUS HAVING A WOUND CLOSURE MATERIAL APPLICATOR ASSEMBLY

(71) Applicant: COVIDIEN LP, Mansfield, MA (US)

(72) Inventor: Frank J. Viola, Sandy Hook, CT (US)

(73) Assignee: Covidien LP, Mansfield, MA (US)

(*) Notice: Subject to any disclaimer, the term of this patent is extended or adjusted under 35 U.S.C. 154(b) by 426 days.

(21) Appl. No.: 13/751,651

(22) Filed: Jan. 28, 2013

(65) Prior Publication Data

US 2013/0144333 A1  Jun. 6, 2013

Related U.S. Application Data

(63) Continuation of application No. 12/820,499, filed on Jun. 22, 2010, now Pat. No. 8,388,652, which is a continuation of application No. 11/108,270, filed on Apr. 18, 2005, now Pat. No. 7,744,628, which is a continuation of application No. 10/513,585, filed as application No. PCT/US03/14700 on May 9, 2003, now Pat. No. 7,431,730.

(60) Provisional application No. 60/379,956, filed on May 10, 2002.

(51) Int. Cl.
*A61B 17/08* (2006.01)
*A61B 17/10* (2006.01)
(Continued)

(52) U.S. Cl.
CPC ......... *A61B 17/068* (2013.01); *A61B 17/00491* (2013.01); *A61B 17/0686* (2013.01); *A61B 17/072* (2013.01); *A61B 17/07207* (2013.01); *A61B 17/07292* (2013.01); *A61B 2017/00884* (2013.01); *A61B 2017/00893* (2013.01); *A61B 2017/07214* (2013.01); *A61B 2017/07285* (2013.01); *A61B 2017/320052* (2013.01)

(58) Field of Classification Search
CPC ........... A61B 17/00491; A61B 17/068; A61B 17/0686; A61B 17/072; A61B 17/07207; A61B 17/07292; A61B 2017/00884; A61B 2017/00893; A61B 2017/07214; A61B 2017/07285; A61B 2017/320052
See application file for complete search history.

(56) References Cited

U.S. PATENT DOCUMENTS 3,079,606 A  3/1963  Bobrov et al.
3,490,675 A  1/1970  Green et al.
(Continued)

FOREIGN PATENT DOCUMENTS

DE  199 24 311 A1  11/2000
EP  0 577 373 A2  1/1994
(Continued)

OTHER PUBLICATIONS

International Search Report corresponding to International Application No. PCT/US03/14700, dated Sep. 9, 2003; (3 pages).
(Continued)

*Primary Examiner* — Julian W Woo

(57) ABSTRACT

This disclosure relates to surgical stapling apparatus for enhancing one or more properties of body tissue that is or is to be repaired or joined. The apparatus includes a staple anvil, a staple cartridge, a driving member for driving the surgical staples from individual staple slots in the staple cartridge and against the staple anvil, and a wound closure material applicator assembly. The applicator assembly includes at least one conduit extending along at least a length of the driving member, anvil and/or cartridge and at least one reservoir in fluid communication with the at least one conduit, the reservoir containing a wound closure material therein. The staples can be coated with a wound closure material.

20 Claims, 22 Drawing Sheets

(51) Int. Cl.
*A61B 17/068* (2006.01)
*A61B 17/00* (2006.01)
*A61B 17/072* (2006.01)
*A61B 17/32* (2006.01)

(56) References Cited

U.S. PATENT DOCUMENTS

| | | |
|---|---|---|
| 3,499,591 A | 3/1970 | Green |
| 4,392,493 A | 7/1983 | Niemeijer |
| 4,429,695 A | 2/1984 | Green |
| 4,573,468 A | 3/1986 | Conta et al. |
| 4,672,969 A | 6/1987 | Dew |
| 5,065,929 A | 11/1991 | Schulze et al. |
| 5,104,025 A | 4/1992 | Main et al. |
| 5,119,983 A | 6/1992 | Green et al. |
| 5,156,614 A | 10/1992 | Green et al. |
| 5,385,606 A | 1/1995 | Kowanko |
| 5,403,312 A | 4/1995 | Yates et al. |
| 5,415,159 A | 5/1995 | Ortiz et al. |
| 5,417,687 A | 5/1995 | Nardella et al. |
| 5,431,322 A | 7/1995 | Green et al. |
| 5,531,744 A | 7/1996 | Nardella et al. |
| 5,542,594 A | 8/1996 | McKean et al. |
| 5,549,628 A | 8/1996 | Cooper et al. |
| 5,575,803 A | 11/1996 | Cooper et al. |
| 5,582,834 A | 12/1996 | Leung et al. |
| 5,599,350 A | 2/1997 | Schulze et al. |
| 5,624,452 A | 4/1997 | Yates |
| 5,658,279 A | 8/1997 | Nardella et al. |
| 5,669,934 A | 9/1997 | Sawyer |
| 5,688,270 A | 11/1997 | Yates et al. |
| 5,690,675 A | 11/1997 | Sawyer et al. |
| 5,693,051 A | 12/1997 | Schulze et al. |
| 5,702,409 A | 12/1997 | Rayburn et al. |
| 5,709,680 A | 1/1998 | Yates et al. |
| 5,716,366 A | 2/1998 | Yates |
| 5,735,848 A | 4/1998 | Yates et al. |
| 5,752,965 A | 5/1998 | Francis et al. |
| 5,755,717 A | 5/1998 | Yates et al. |
| 5,769,892 A | 6/1998 | Kingwell |
| 5,782,914 A | 7/1998 | Schankereli |
| 5,799,857 A | 9/1998 | Robertson et al. |
| 5,807,393 A | 9/1998 | Williamson, IV et al. |
| 5,810,811 A | 9/1998 | Yates et al. |
| 5,810,855 A | 9/1998 | Rayburn et al. |
| 5,814,057 A | 9/1998 | Oi et al. |
| 5,817,091 A | 10/1998 | Nardella et al. |
| 5,817,093 A | 10/1998 | Williamson, IV et al. |
| 5,833,690 A | 11/1998 | Yates et al. |
| 5,833,695 A | 11/1998 | Yoon |
| 5,876,401 A | 3/1999 | Schulze et al. |
| 5,915,616 A | 6/1999 | Viola et al. |
| 5,964,394 A | 10/1999 | Robertson |
| 6,003,517 A | 12/1999 | Sheffield et al. |
| 6,024,741 A | 2/2000 | Williamson, IV et al. |
| 6,032,849 A | 3/2000 | Mastri et al. |
| 6,045,560 A | 4/2000 | McKean et al. |
| 6,063,097 A | 5/2000 | Oi et al. |
| 6,099,551 A | 8/2000 | Gabbay |
| H1904 H | 10/2000 | Yates et al. |
| 6,165,175 A | 12/2000 | Wampler et al. |
| 6,239,190 B1 | 5/2001 | Wilkinson et al. |
| 6,241,139 B1 | 6/2001 | Milliman et al. |
| 6,250,532 B1 | 6/2001 | Green et al. |
| 6,273,897 B1 | 8/2001 | Dalessandro et al. |
| 6,296,640 B1 | 10/2001 | Wampler et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,468,275 B1 | 10/2002 | Wampler et al. |
| 6,485,490 B2 | 11/2002 | Wampler et al. |
| 6,488,197 B1 | 12/2002 | Whitman |
| 6,491,201 B1 | 12/2002 | Whitman |
| 6,503,257 B2 | 1/2003 | Grant et al. |
| 6,569,173 B1 | 5/2003 | Blatter et al. |
| 6,592,597 B2 | 7/2003 | Grant et al. |
| 6,638,285 B2 | 10/2003 | Gabbay |
| 6,656,193 B2 | 12/2003 | Grant et al. |
| 6,681,979 B2 | 1/2004 | Whitman |
| 6,695,199 B2 | 2/2004 | Whitman |
| 7,238,195 B2 | 7/2007 | Viola |
| 7,431,730 B2 | 10/2008 | Viola |
| 7,942,302 B2 | 5/2011 | Roby et al. |
| 2001/0007069 A1 | 7/2001 | Bombard et al. |
| 2002/0151911 A1 | 10/2002 | Gabbay |
| 2002/0156150 A1 | 10/2002 | Williams et al. |
| 2002/0165559 A1 | 11/2002 | Grant et al. |
| 2002/0165562 A1 | 11/2002 | Grant et al. |
| 2002/0173558 A1 | 11/2002 | Williams et al. |
| 2003/0050590 A1 | 3/2003 | Kirsch |
| 2003/0073982 A1 | 4/2003 | Whitman |
| 2003/0089757 A1 | 5/2003 | Whitman |
| 2003/0183671 A1 | 10/2003 | Mooradian et al. |
| 2004/0093029 A1 | 5/2004 | Zubik et al. |
| 2005/0192628 A1 | 9/2005 | Viola |
| 2006/0085032 A1 | 4/2006 | Viola |

FOREIGN PATENT DOCUMENTS

| | | |
|---|---|---|
| WO | WO 00/56376 A1 | 9/2000 |
| WO | WO 01/62158 A2 | 8/2001 |
| WO | WO 01/62162 A1 | 8/2001 |
| WO | WO 02/30297 A2 | 4/2002 |
| WO | WO 03/055402 A1 | 7/2003 |
| WO | WO 03/088844 A1 | 10/2003 |
| WO | WO 03/088845 A2 | 10/2003 |
| WO | WO 03/094743 A1 | 11/2003 |
| WO | WO 03/094746 A1 | 11/2003 |
| WO | WO 03/105698 A2 | 12/2003 |

OTHER PUBLICATIONS

International Search Report corresponding to European Application No. EP 05 00 4539, dated Feb. 9, 2006; (2 pages).
International Search Report corresponding to International Application No. PCT/US05/37265, dated Apr. 24, 2008; (1 page).
Non-Final Office Action dated Aug. 13, 2007 for U.S. Appl. No. 10/513,585, filed Nov. 3, 2004; (16 Pages).
Final Office Action dated Jan. 29, 2008 for U.S. Appl. No. 10/513,585, filed Nov. 3, 2004; (8 Pages).
Interview Summary for Interview dated May 29, 2008 for U.S. Appl. No. 10/513,585, filed Nov. 3, 2004; (1 Page).

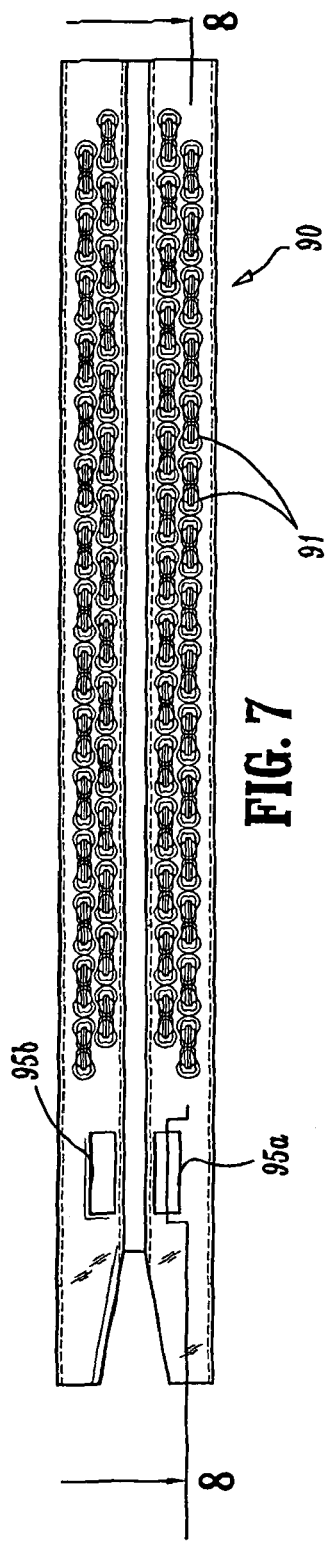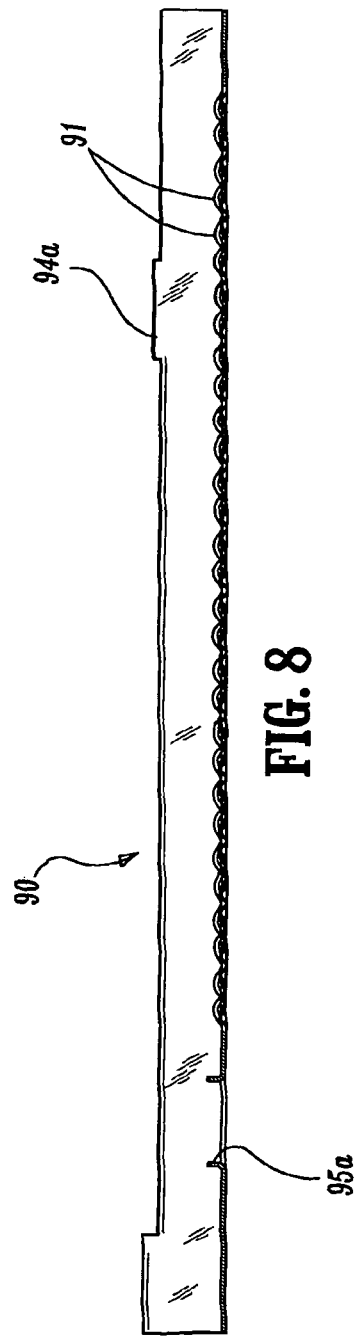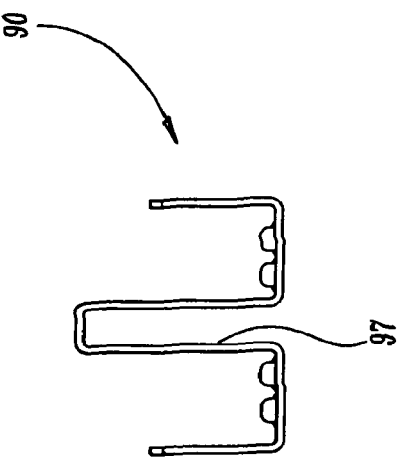

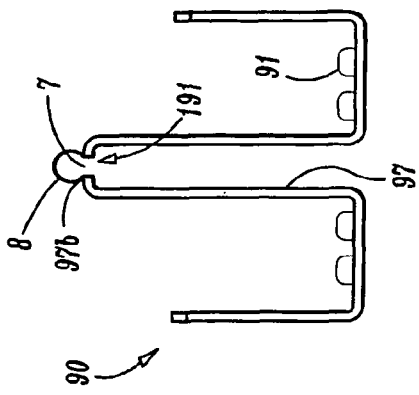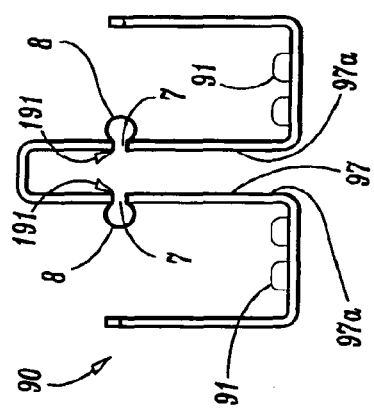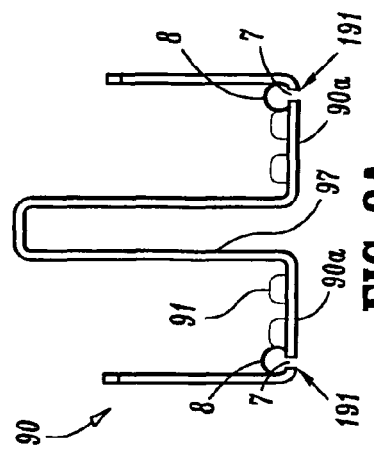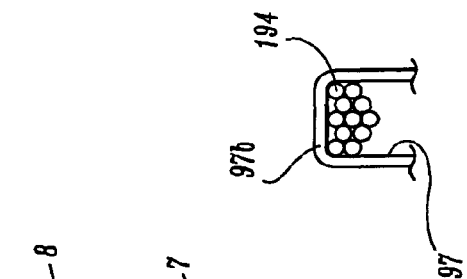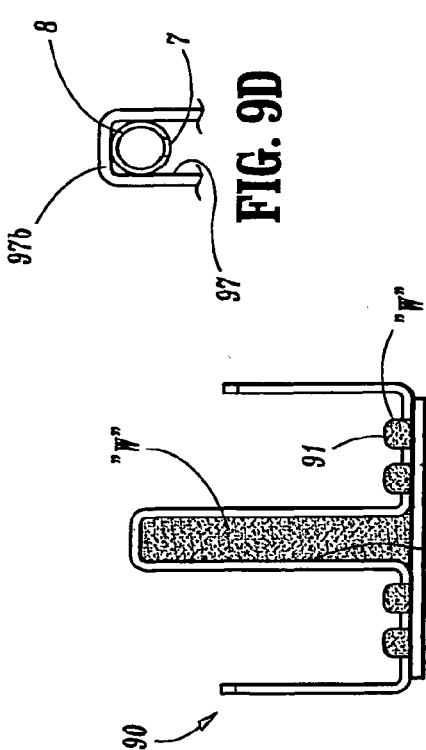

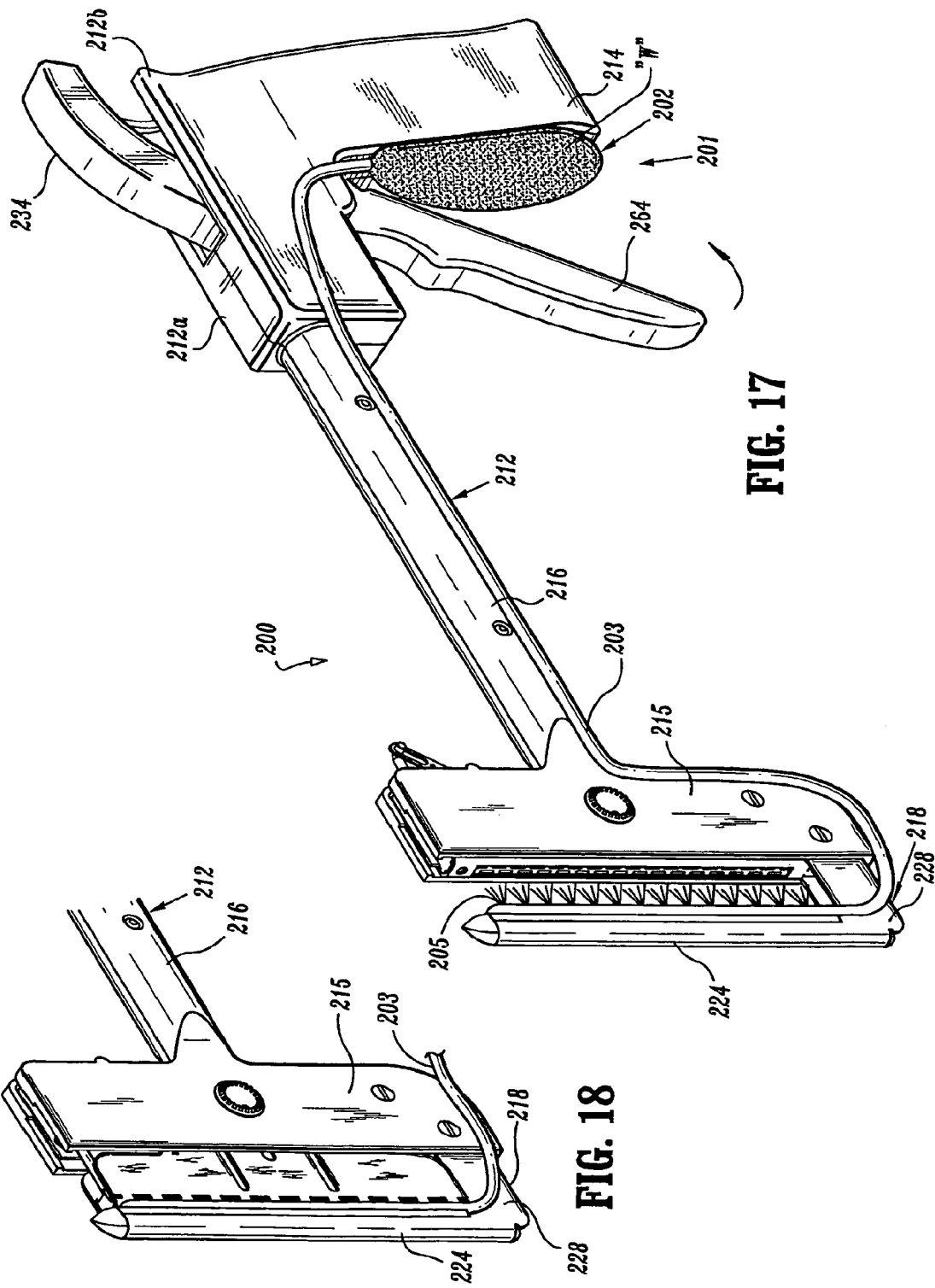

SURGICAL STAPLING APPARATUS HAVING A WOUND CLOSURE MATERIAL APPLICATOR ASSEMBLY

CROSS-REFERENCE TO RELATED APPLICATIONS

The present application is a Continuation Application which claims the benefit of and priority to U.S. patent application Ser. No. 12/820,499 filed on Jun. 22, 2010, (now U.S. Pat. No. 8,388,652) which is a Continuation Application claiming the benefit of and priority to U.S. patent application Ser. No. 11/108,270, filed on Apr. 18, 2005 (now U.S. Pat. No. 7,744,628), which is a Continuation Application claiming the benefit of and priority to U.S. patent application Ser. No. 10/513,585, filed on Nov. 3, 2004 (now U.S. Pat. No. 7,431,730), which is a National Phase filing under 35 U.S.C. 371 of International Application Serial No. PCT/US03/014700, filed on May 9, 2003, claiming the benefit of and priority to U.S. Provisional Application Ser. No. 60/379,956 filed on May 10, 2002, the entire contents each of which being incorporated herein by reference.

BACKGROUND

1. Technical Field

This disclosure relates to surgical stapling apparatus, and more particularly, to a surgical stapling apparatus having a wound closure material applicator assembly for applying a plurality of surgical fasteners to body tissue and dispensing a quantity of wound closure material, such as an astringent, to reduce and/or prevent staple line and/or knife cut line bleeding.

2. Background of Related Art

Surgical procedures requiring cutting of tissue can result in bleeding at the site of the cutting. Various techniques have been developed to control bleeding with varying degrees of success such as, for example, suturing, applying clips to blood vessels, and using surgical fasteners, as well as electrocautery and other tissue healing techniques.

Surgical instruments using surgical fasteners entail grasping or clamping tissue between opposing jaw structure and then joining the tissue by employing the surgical fasteners. These instruments are well known in the art. In some instruments a knife is provided to cut the tissue which has been joined by the fasteners. The fasteners are typically in the form of surgical staples however, two part polymeric fasteners can also be utilized.

Instruments for this purpose can include two elongated or circular members which are respectively used to capture or clamp tissue. Typically, one of the members carries a cartridge which houses a plurality of staples arranged in at least two lateral rows while the other member carries an anvil which defines a surface for forming the staple legs as the staples are driven from the cartridge. Where two part fasteners are used, one of the members carries a cartridge which houses one half of a fastener while the other member carries the second part of the fastener, e.g., the mating part, which halves are configured and adapted to be held together upon approximation. Typically, the stapling operation is effected by a drive member which travels longitudinally through the cartridge carrying member, with the drive member acting upon the pushers which engage the staples to sequentially eject them from the cartridge. A knife can be provided which travels between the staple rows to longitudinally cut (i.e., form a knife cut line) and/or open the stapled tissue between the rows of staples. Usually, but not always, the knife is associated with or travels with the staple drive member. Such instruments are disclosed in U.S. Pat. Nos. 3,079,606 and 3,490,675, the entire contents of which are incorporated herein by reference.

A later stapler disclosed in U.S. Pat. No. 3,499,591, the entire contents of which are incorporated herein by reference, applies a double row of staples on each side of the incision or the knife cut line. This is accomplished by providing a cartridge assembly in which a cam member moves through an elongate guide path between two sets of staggered staple carrying grooves. Staple drive members are located within the grooves and are positioned in such a manner so as to be contacted by the longitudinally moving cam to effect ejection of the staples. Other examples of staplers are disclosed in U.S. Pat. Nos. 4,429,695, 5,065,929 and 5,156,614, the entire contents of which are incorporated herein by reference.

Electrocautery devices are preferred in certain surgical procedures for effecting improved hemostasis by heating tissue and blood vessels using thermogenic energy, preferably radiofrequency energy, to cause coagulation or cauterization. Monopolar devices utilize one electrode associated with a cutting or cauterizing instrument and a remote return electrode, usually adhered externally to the patient. Bipolar instruments utilize two electrodes and the cauterizing current is generally limited to tissue between the two electrodes of a tissue treating portion (e.g., end effector) of an instrument.

Even though stapling apparatus and electrocauterizing apparatus and techniques respectively are generally well suited to control bleeding along the knife cut line, other apparatus and techniques are herein envisioned.

Therefore, it is an aspect of the present disclosure to provide a surgical stapling apparatus that provides general hemostatis, tissue joining or welding, and also applies a wound closure material to body tissue that enhances one or more properties of the body tissue that is or is to be repaired or joined, for example, hemostatis along a cut line formed by a knife or other cutting means and/or along a staple line to reduce or prevent bleeding along the cut line and/or staple line.

SUMMARY

The present disclosure relates to surgical stapling apparatus, and more particularly, to a surgical stapling apparatus having a wound closure material applicator assembly for applying a plurality of surgical fasteners to body tissue and dispensing a wound closure material, such as an astringent, to prevent staple line and knife cut line bleeding.

According to one aspect of the present disclosure, a surgical stapling apparatus for enhancing one or more properties of body tissue that is or is to be repaired or joined is provided. The surgical stapling apparatus includes a staple anvil positioned on a distal end of the stapling apparatus and having a working surface and a staple cartridge positioned adjacent a distal end of the stapling apparatus and juxtaposable relative to the staple anvil. The staple cartridge includes a working surface, one or more rows of individual staple slots formed in the working surface, and a plurality of surgical staples individually disposed within the individual staple slots. The staple apparatus further includes a driving member for firing the surgical staples from the individual staple slots and against the staple anvil and a wound closure material applicator assembly operatively associated with the stapling apparatus. The wound closure applicator assembly includes at least one conduit extending along at least a length of the driving member, and at least one reservoir in fluid communication with the at least one conduit, the reservoir being for containing a wound closure material therein, and the conduit having at least one opening and being adapted to provide wound closure material therethrough to an area between the working surface of the staple anvil and the staple cartridge.

The at least one conduit can include a plurality of openings formed therein for dispensing the wound closure material therefrom. Longitudinal translation of the driving member causes longitudinal translation of the at least one conduit across at least some of the individual staple slots, such that at least one of the plurality of openings is in communication with at least one of the staple slots.

It is envisioned that the at least one reservoir can be compressible. Accordingly, compression of the at least one reservoir causes the wound closure material to be dispensed from the at least one opening of the at least one conduit. It is contemplated that the apparatus includes a compression member that effects the compression of the at least one reservoir.

The wound closure material can be an astringent, a sulphate of aluminum, an adhesive, a hemostat and/or a sealant.

The at least one conduit can be positioned across at least some of the individual staple slots such that compression of the at least one reservoir dispenses the wound closure material through the at least some staple slots.

In an embodiment, each of the plurality of surgical staples is coated with the wound closure material.

The driving member can include a pair of elongate beams, and the applicator assembly can include a pair of conduits extending, one each, along a length of the respective beams. Each of the pair of conduits can have at least one opening therein and being in fluid communication with the at least one reservoir. Each of the pair of conduits includes a plurality of openings formed therein. Longitudinal translation of the driving member causes longitudinal translation of the pair of conduits, such that at least one of the plurality of openings is in communication with at least one of the staple slots.

It is envisioned that the wound closure material is an astringent, an adhesive, a hemostat and/or a sealant.

It is envisioned that when the pair of conduits is positioned across at least some of the individual staple slots, compression of the at least one reservoir dispenses the wound closure material through the at least some staple slots.

Each of the plurality of staples can be coated with wound closure material.

According to another aspect of the present disclosure, a surgical stapling apparatus for enhancing one or more properties of body tissue that is or is to be repaired or joined is provided and includes a staple cartridge positioned adjacent a distal end of the stapling apparatus, and a plurality of surgical staples disposed within the staple cartridge, the surgical staples being coated with a wound closure material.

The wound closure material can be an astringent, an adhesive, a hemostat and a sealant.

According to yet another aspect of the present disclosure a disposable loading unit for use with a surgical stapling apparatus for enhancing one or more properties of body tissue that is or is to be repaired or joined, the surgical stapling apparatus being of the type having a frame, a first shaft having a distal end, and an actuation mechanism to drive a drive member distally through the shaft is provided. The disposable loading unit includes an elongated shaft having a distal end and a proximal end adapted to be operably connected to the distal end of the first shaft, a staple anvil positioned on a distal end of the elongated shaft and having a working surface, and a staple cartridge positioned adjacent a distal end of the elongated shaft and juxtaposable relative to the staple anvil. The staple cartridge includes a working surface, one or more rows of individual staple slots formed in the working surface, and a plurality of surgical staples individually disposed within the individual staple slots, and at least one conduit extending along at least a length of the removable staple cartridge.

The at least one conduit can be adapted to be in fluid communication with at least one reservoir, the reservoir being for containing a wound closure material. The at least one conduit can include at least one aperture formed therein.

The reservoir is formed of a compressible material, wherein compression of the reservoir will dispense the wound closure material from the at least one aperture formed in the at least one conduit.

It is envisioned that the plurality of staples are coated with wound closure material.

The wound closure material can be an astringent, an adhesive, a hemostat and a sealant.

The disposable loading unit can include a pair of conduits extending, one each, along lateral sides of the staple cartridge. The pair of conduits are preferably in proximity to the working surface.

It is envisioned that the working surface can be provided with a series of apertures formed along a length thereof and wherein the wound closure material is dispensed through the apertures formed in the length of the working surface.

The disposable loading unit can be used in a surgical stapling apparatus for performing an open gastrointestinal anastomosis surgical procedure or endoscopic or laparoscopic gastrointestinal surgical procedures.

In yet another aspect of the present disclosure, a surgical staple cartridge configured and adapted to be removably received within a surgical stapler is provided. The staple cartridge includes a working surface, one or more laterally spaced apart rows of staple slots formed in the working surface, a plurality of surgical staples disposed, one each, within the staple slots for mechanically securing adjacent layers of body tissue to one another, and at least one conduit extending along at least a length of the staple cartridge, the at least one conduit having a plurality of openings along the majority of the length of the conduit and being adapted such that the plurality of openings can communicate with a plurality of the staple slots, the conduit having a connection for connection to a supply of wound closure material.

The connection can be fluidly connectable to at least one reservoir for containing the wound closure material therein. The plurality of apertures preferably includes a plurality of microtubes.

The reservoir can be formed of a compressible material, such that compression of the reservoir will dispense a wound closure material from the reservoir through the apertures formed in the at least one conduit.

Each of the plurality of staples is preferably coated with wound closure material. The wound closure material can be an astringent, an adhesive, a hemostat and/or a sealant.

The surgical staple cartridge can include a pair of conduits extending, one each, along walls of the removable staple cartridge. The pair of conduits are in proximity to the working surface.

The working surface can be provided with a series of apertures formed along a length thereof and wherein the wound closure material is dispensed through the apertures formed in the length of the working surface.

In still a further aspect of the present disclosure, a surgical stapling apparatus for enhancing one or more properties of body tissue that is or is to be repaired or joined is provided. The surgical stapling apparatus includes a staple anvil positioned on a distal end of the stapling apparatus. The staple anvil includes a working surface, a longitudinal cavity formed in the working surface, a plurality of staple forming recesses formed in the working surface, and a wound closure material retained in at least a length of the staple anvil for dispensing wound closure material into, onto the body tissue.

The wound closure material is preferably retained in the longitudinal cavity. It is envisioned that the longitudinal cavity can be a knife track.

It is contemplated that the surgical stapling apparatus can include a knife blade operatively connected thereto, wherein the knife blade is coated with a wound closure material.

Further features of the surgical stapling apparatus of the present disclosure will become more readily apparent to those skilled in the art from the following detailed description taken in conjunction with the drawings.

BRIEF DESCRIPTION OF THE DRAWINGS

Various embodiments of the surgical stapling apparatus of the invention will be described hereinbelow with reference to the drawings wherein:

FIG. 7 is a plan view of the preformed anvil plate which is mounted to the anvil support beam of the anvil half-section of the surgical stapling apparatus shown in FIG. 1A;

FIG. 8 is a cross-sectional view of the preformed anvil plate taken along line 8-8 of FIG. 7;

FIG. 9 is a front end view of the preformed anvil plate illustrated in FIGS. 7 and 8;

FIGS. 9A-9G are front end views of preformed anvil plates including wound closure material applicator systems operatively associated therewith;

FIG. 17 is a perspective view of an alternative surgical stapling apparatus having a wound closure material applicator assembly operatively associated therewith;

FIG. 18 is a perspective view of a distal end of the surgical stapling apparatus of FIG. 17;

DETAILED DESCRIPTION OF PREFERRED EMBODIMENTS

Figure 1A:
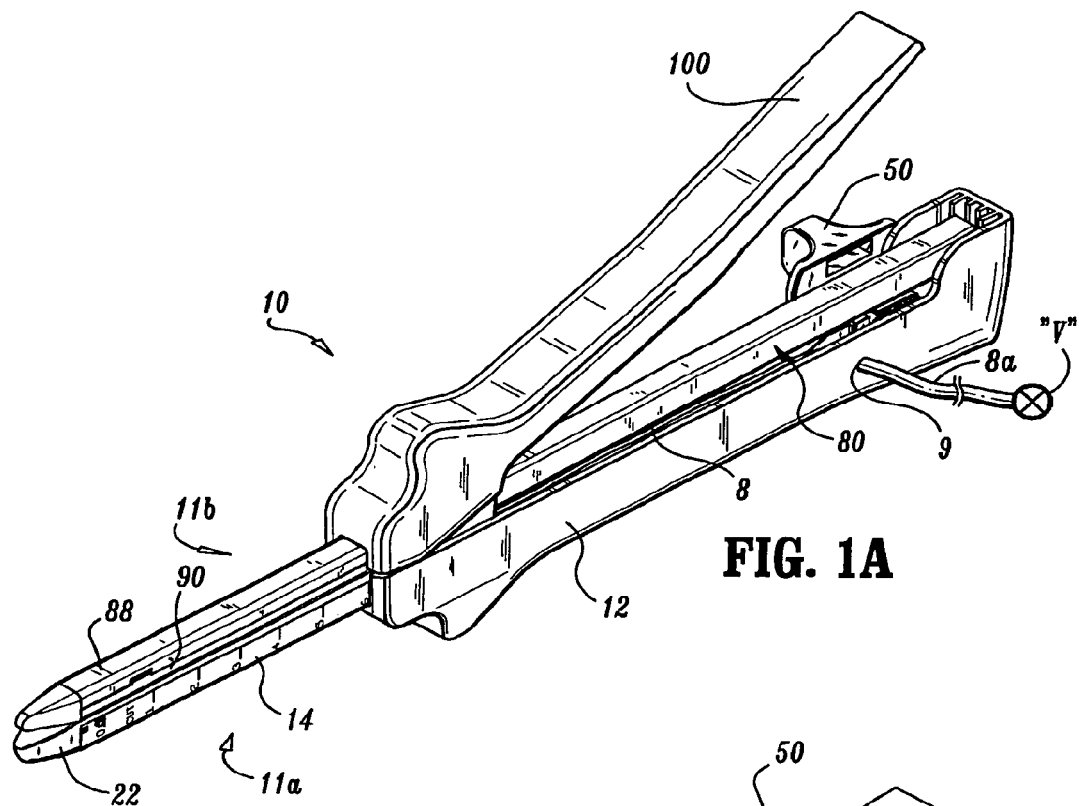
FIG. 1A is a perspective view of a surgical stapling apparatus including a wound closure material applicator assembly constructed in accordance with a preferred embodiment, with the clamping handle of the apparatus disposed in an upright open position.

Preferred embodiments of the presently disclosed surgical stapling apparatus will now be described with reference to the drawing figures wherein like reference numerals identify similar or identical elements. In the drawings and in the following description, the term "proximal", as is traditional, will refer to the end of the apparatus which is closer to the operator, while the term "distal" will refer to the end of the apparatus which is further from the operator.

The present invention provides a surgical stapling apparatus having a wound closure material applicator assembly which applies to body tissue at least one wound closure material, for example, an astringent, which causes small blood vessels to constrict or close, or a coagulant to help the blood to coagulate, as well as surgical fasteners or staples for providing hemostasis, tissue joining or welding. The use of at least one wound closure material for example can provide short, i.e., temporary, and long-term, i.e., permanent, hemostasis and sealing, and reduce or prevent bleeding along a staple line and/or a knife cut line, while the fastening or stapling feature provides short and long-term tissue strength and hemostasis.

Since staple line and knife cut line bleeding is reduced or prevented, the surgical stapling apparatus of the present invention makes it possible to expand the applicable range of specific staple sizes to include thinner or, thicker staples used in highly vascularized tissue. For example, it is contemplated that relatively large-size staples could be used with the surgical stapling apparatus of the present invention to join thin, highly vascularized tissue.

Figure 1B:
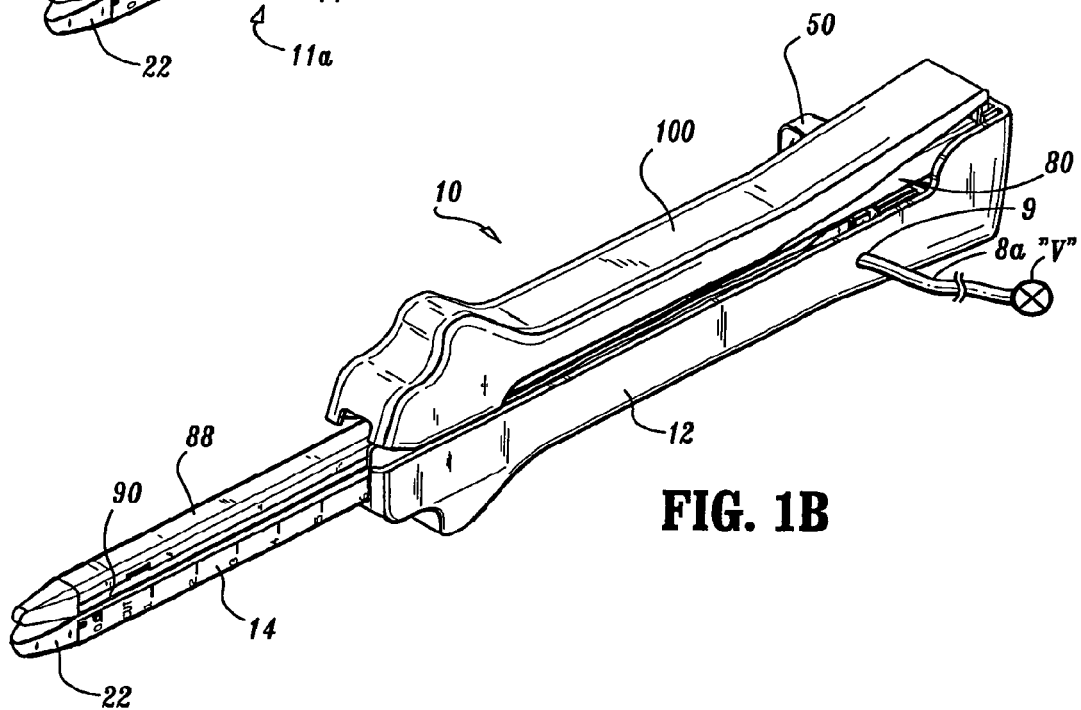
FIG. 1B is a perspective view of the surgical stapling apparatus illustrated in FIG. 1A with the clamping handle disposed in a closed position.

Referring now to the drawings wherein like reference numerals identify similar structural elements, there is illustrated in FIGS. 1A and 1B a surgical stapling apparatus, in accordance with a preferred embodiment of the present disclosure, is designated generally as reference numeral 10. Surgical stapling apparatus 10 includes a cartridge half-section 11a and an anvil half-section 11b.

Figure 2A:
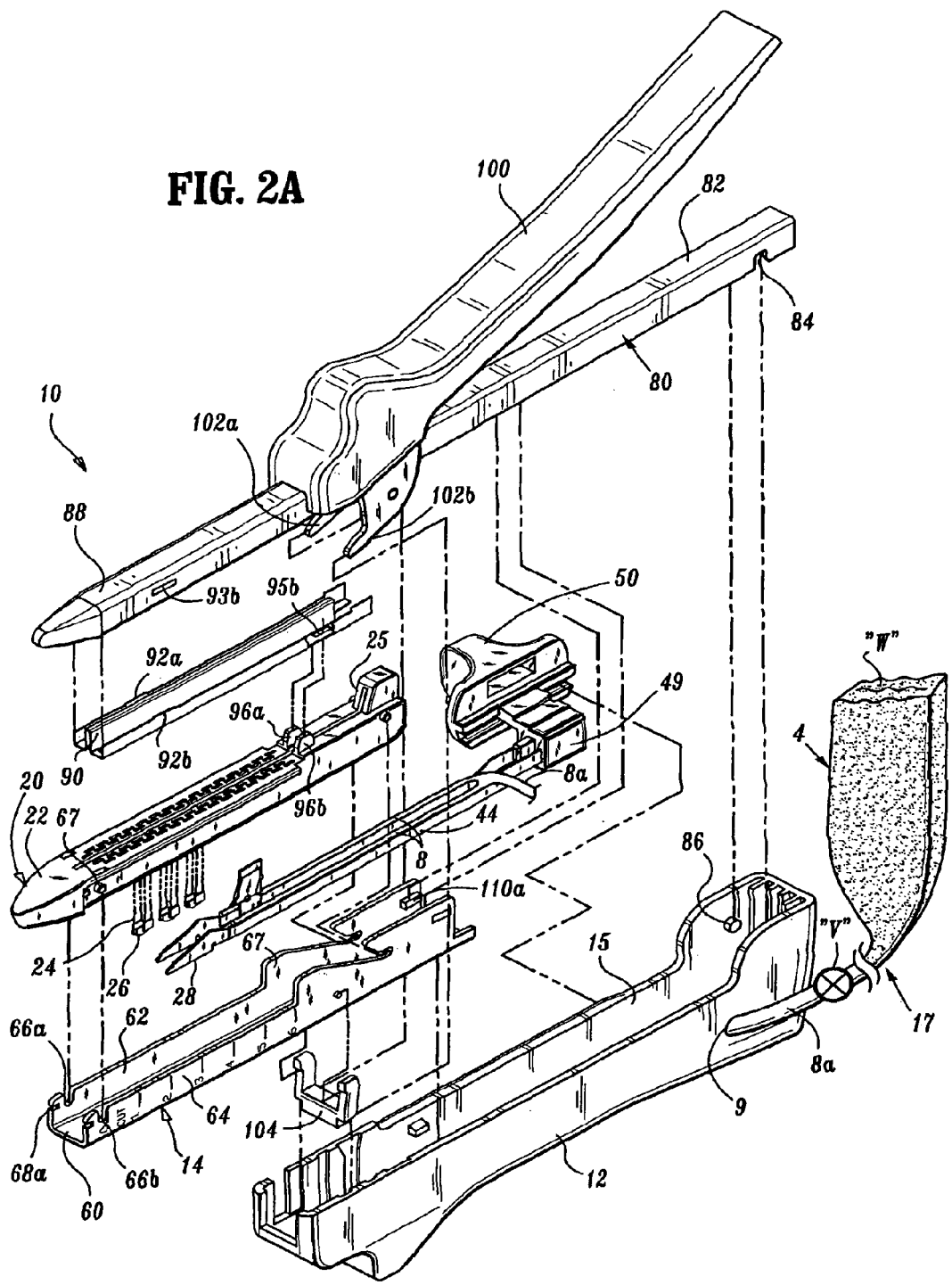
FIG. 2A is an exploded perspective view of the surgical stapling apparatus of FIG. 1A.
Figure 2B:
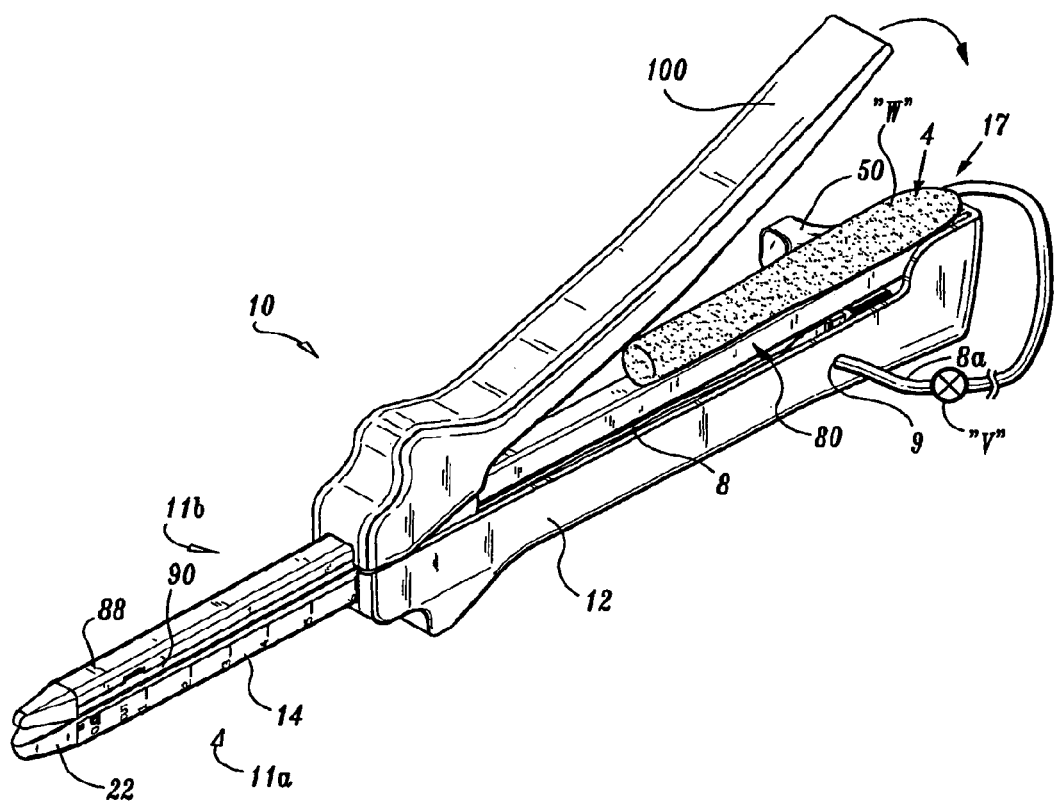
FIG. 2B is a perspective view of a surgical stapling apparatus having a wound closure material applicator assembly constructed in accordance with another preferred embodiment.
Figure 3:
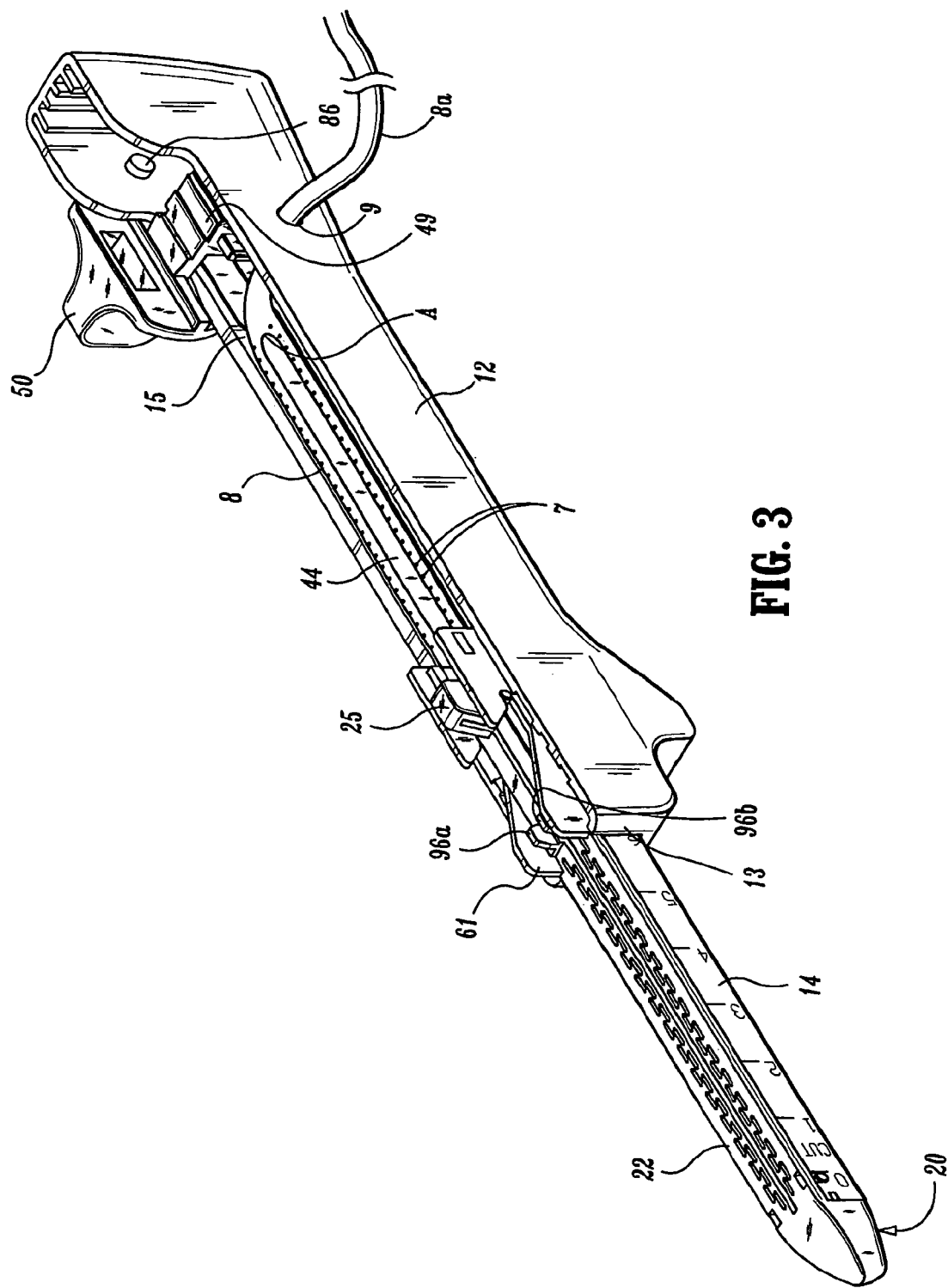
FIG. 3 is a perspective view of a cartridge half-section of the surgical stapling apparatus of FIG. 1A.
Figure 4A:
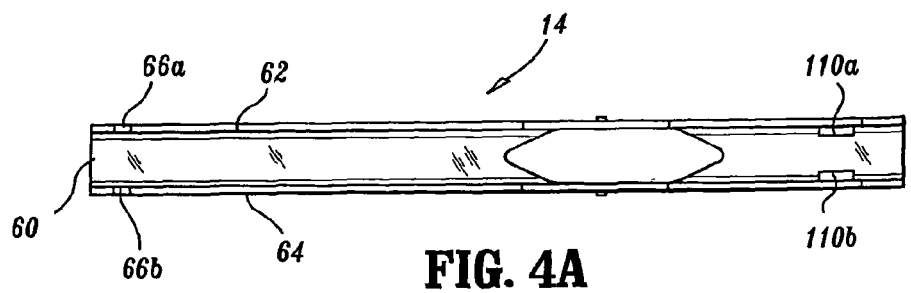
FIG. 4A is a top plan view of a retention channel of the surgical stapling apparatus of FIG. 1A.
Figure 4B:
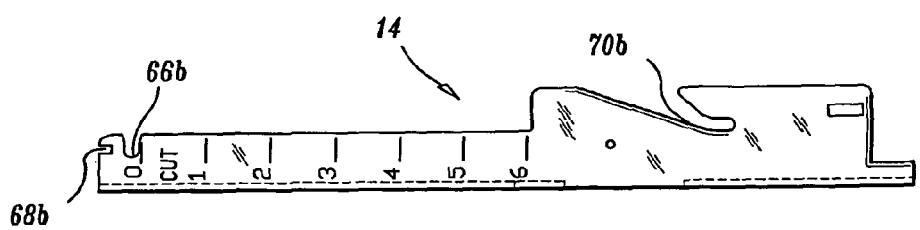
FIG. 4B is a side elevational view of the retention channel shown in FIG. 4A.
Figure 4C:
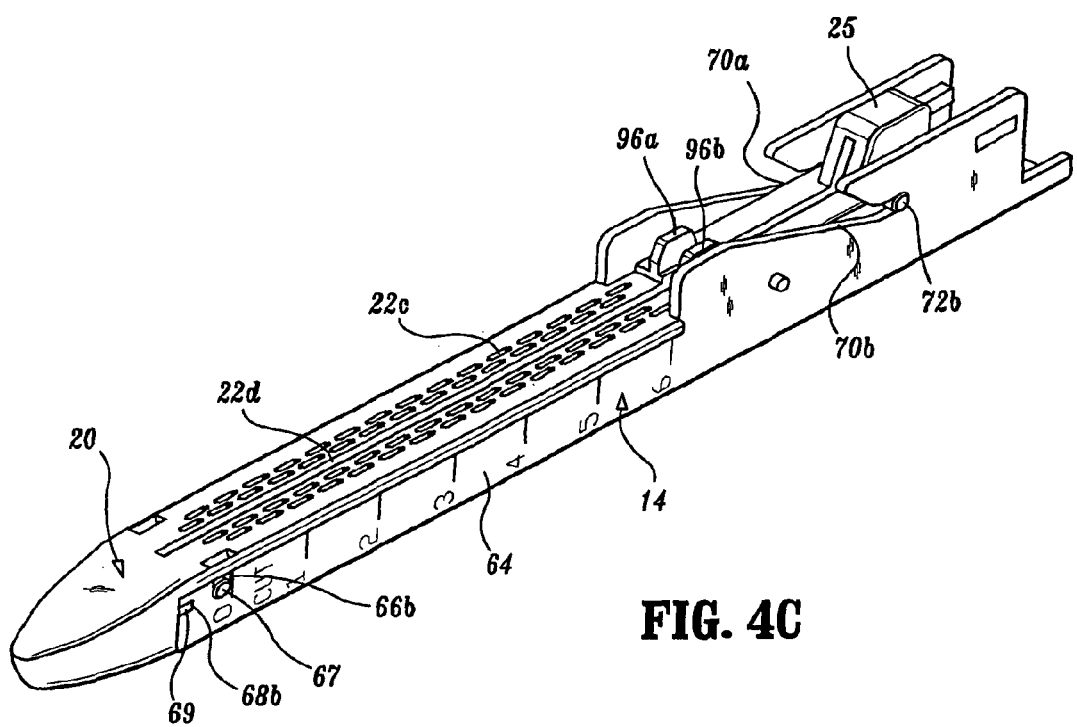
FIG. 4C is a perspective view of the retention channel of FIGS. 4A and 4B with a disposable loading unit retained therein.

Referring to FIGS. 2A, 2B and 3, stapling apparatus 10 includes a body portion 12 defining a handle for grasping and supporting the stapling apparatus 10. A retaining channel 14 is mounted in the interior cavity 15 of body portion 12 adjacent the distal end thereof. Retaining channel 14 is dimensioned and configured to support a disposable loading unit 20, as illustrated in FIG. 4C.

Figure 5A:
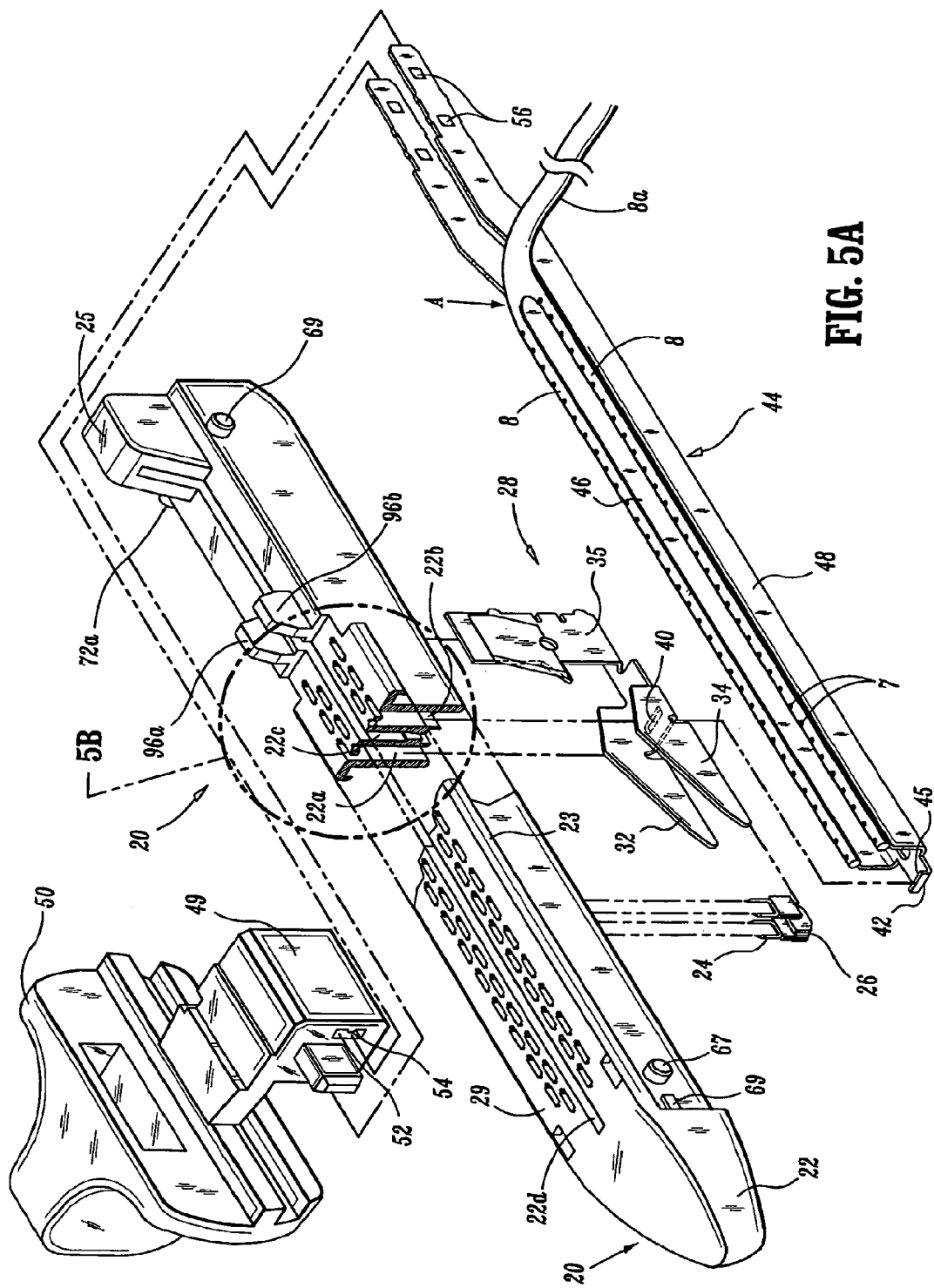
FIG. 5A is an enlarged perspective view, with parts separated, of the disposable loading unit and actuation assembly of the surgical stapling apparatus of FIG. 1A.

As shown in FIG. 5A, disposable loading unit 20 includes a cartridge 22 having a tissue contacting or working surface 29, a plurality of slots 22c which support a corresponding number of surgical staples 24, a plurality of staple pushers or ejectors 26 adapted and configured to eject staples 24 from the slots 22c when acted upon by a staple driving force. Stapling apparatus 10 further includes an actuation sled 28 slidably disposed in retention channel 14 (see FIG. 2A) to translate through cartridge 22 in a longitudinal direction to transmit a staple driving force to ejectors 26.

According to a preferred embodiment of the invention, surgical staples 24 are preferably coated (understood to include treated) with at least one wound closure material, such as an astringent, e.g., a sulphate of aluminum, which causes small blood vessels to close and helps the blood to coagulate. It is provided that the astringent used could be that provided in the material commercially available under the trade designation No Nix Styptic Pencils from Requa, Inc.

Cartridge 22 is preferably fabricated from liquid crystal polymer material, such as liquid crystal polymer resin, commercially available from Plasticsnet.com under the trademark Xydar, although other materials are contemplated. Cartridge 22 has a lip 23 which engages retention channel 14 to prevent inward rotation of cartridge 22 (see FIG. 5B).

Figure 6A:
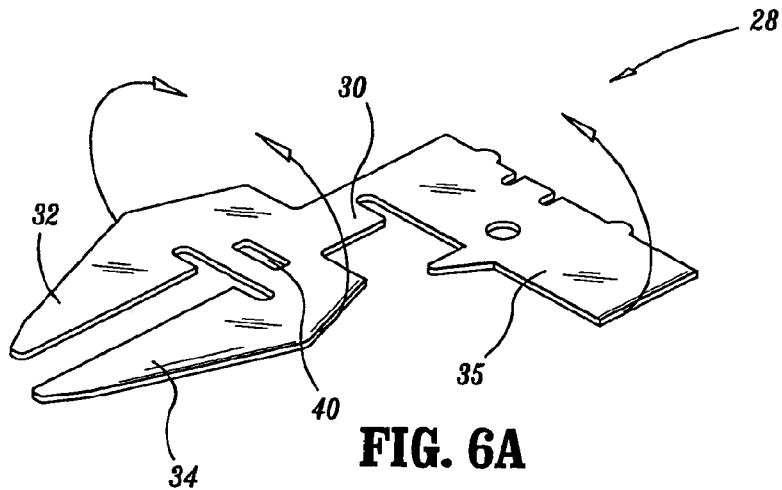
FIG. 6A is a perspective view of the actuation sled of the disposable loading unit shown in FIG. 5A in a pre-formed condition.
Figure 6B:
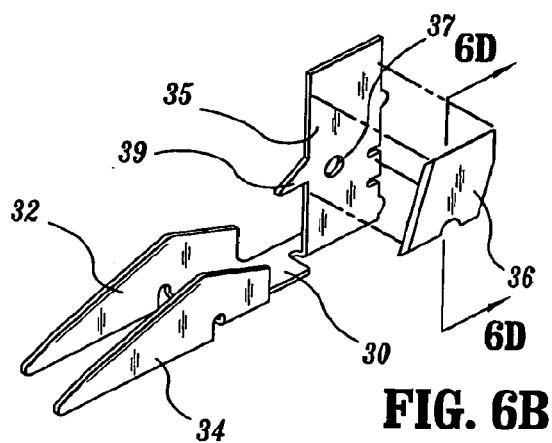
FIG. 6B is a perspective view of the actuation sled shown in FIG. 6A in a formed condition with the knife blade separated therefrom for illustrative purposes.
Figure 6D:
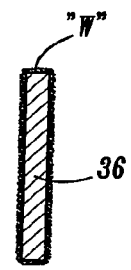
FIG. 6D is an enlarged cross-sectional view of a knife blade, in accordance with the present disclosure, as taken through line 6D-6D of FIG. 6B.
Figure 6C:
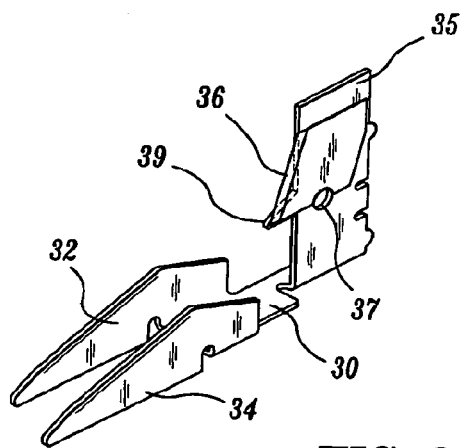
FIG. 6C is a perspective view of the formed actuation sled shown in FIG. 6B with the knife blade mounted to the blade support portion thereof.

As best seen in FIG. 6A, actuation sled 28 is preferably monolithically formed from a single piece of sheet metal which is folded into the desired structural configuration shown in FIGS. 6B and 6C. In this configuration, actuation sled (staple actuator) 28 defines a base portion 30, two upstanding cam wedges 32 and 34, and an upstanding shank 35 which supports a knife blade 36. Knife blade 36 is preferably spot welded to shank 35, although other known fastening methods, e.g., clamping, may be employed. As illustrated in FIG. 6B, a weldment port 37 and a winglet 39 are provided to facilitate the proper alignment and cohesion of knife blade 36 to shank 35 during fabrication. Actuation sled 28 can also be non-monolithically formed.

Figure 6E:
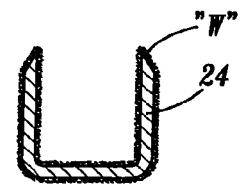
FIG. 6E is an enlarged cross-sectional view of a surgical staple, in accordance with the present disclosure.

According to another embodiment of the invention, as seen in FIGS. 6D and 6E, knife blade 36 is preferably itself, or in combination with staples 24, treated or coated with at least one wound closure material "W", such as an astringent, e.g., a sulfate of aluminum. In such cases, the at least one wound closure material "W" can be a particulate, preferably a powder or coating, which has been coated on knife blade 36 and staples 24. In particular apparatus, the at least one wound closure material "W" preferably is fluid soluble (i.e., water soluble) or activatable upon exposure to fluid (e.g., water, saline, blood, etc.).

Cam wedges 32 and 34 are longitudinally staggered with respect to one another so that one leads the other throughout the sled's translation through cartridge 22. As shown in FIG. 5A, longitudinal slots 22a and 22b accommodate the longitudinal translation of cam wedges 32 and 34, while slot 22d accommodates the longitudinal translation of shank 35.

The base portion 30 of actuation sled 28 has a transverse slot 40 defined therein which is dimensioned and configured to releasably retain an upturned flange 42 formed at the distal end of elongated driving member, here, actuation channel 44 (FIG. 5A). When the disposable loading unit 20 is placed into retaining channel 14 and actuation sled 28 is disposed in its proximal-most position, flange 42 releasably engages slot 40. Thus, movement of actuation channel 44 moves actuation sled 28. After a stapling operation, when disposable loading unit 20 is removed from the retaining channel, flange 42 is easily disengaged from slot 40.

With continued reference to FIG. 5A, actuation channel 44 is defined by a base portion 45 and two parallel upstanding beams 46 and 48 of elongate configuration. The distal ends of beams 46 and 48 are staggered to match the staggered orientation of cam wedges 32 and 34, respectively. The proximal end of each beam projects rearwardly to engage a mounting block 49 that is associated with firing knob 50. A pair of slots 52 (only one of which is shown) are formed in mounting block 49 for receiving the proximal end of each of the upstanding beams 46, 48 of actuation channel 44 and the slots are provided with detents 54 for engaging apertures 56 in the beam ends to lockingly retain beams 46, 48 in mounting block 49. In use, longitudinal movement of firing knob 50 causes corresponding longitudinal translation of actuation channel 44 and actuation sled 28.

As seen in FIGS. 1A-3, surgical stapling apparatus 10 includes a wound closure material applicator assembly 17 (see FIG. 2B) operatively associated therewith. As seen in FIG. 5A, wound closure material applicator assembly 17 can include two conduits 8 secured to and extending, one each, along an upper edge of beams 46, 48 of actuation channel 44. Each conduit 8 includes a plurality of openings 7 formed along a length thereof, preferably along an upper portion thereof, for dispensing at least one wound closure material "W", preferably upwardly therefrom. In use, longitudinal translation of actuation channel 44 causes longitudinal translation of conduits 8 through staple cartridge 22.

Figure 16:
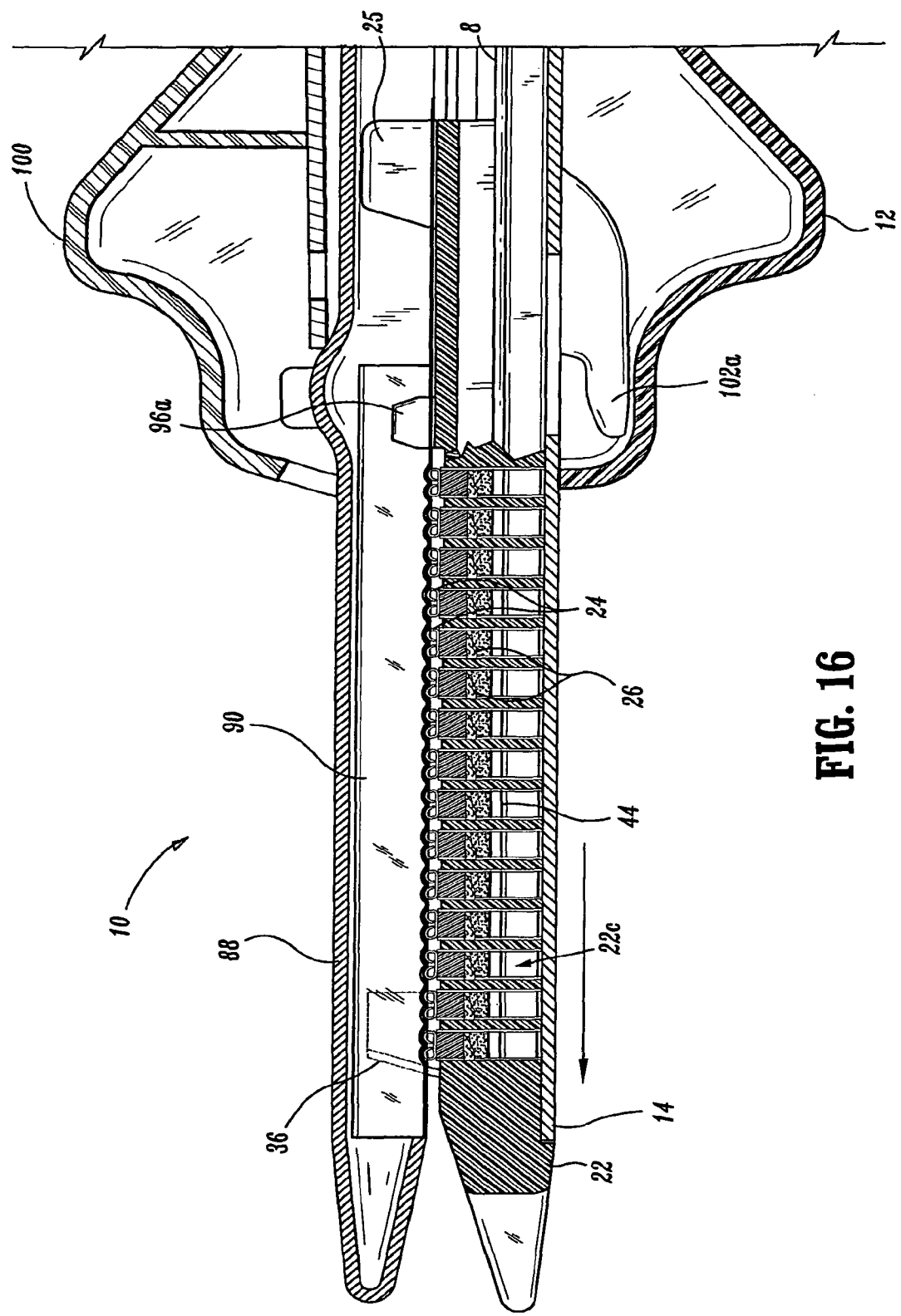
FIG. 16 is a side elevational view in cross-section of the surgical stapling apparatus of the subject application with the actuation sled advanced to the distal end of the cartridge and, illustrating the distribution of a substance at least along at least one staple line at the conclusion of a staple firing procedure.

Conduits 8 have sufficient slack to enable longitudinal movement or extension through body portion 12 and cartridge 22 in order for the at least one wound closure material "W" to be applied along the entire length of a knife cut line formed by knife blade 36 and along at least one staple line formed by surgical staples 24 (see FIG. 16). The conduits 8 are adjoined at location A, as shown by FIGS. 3, 5A, 11 and 12, and form one conduit 8a which exits body portion 12 via an opening 9 (see FIGS. 1A and 1B). Conduit 8a is in fluid communication with at least one reservoir 4 which contains/ stores or is adapted to contain/store at least one wound closure material "W" (see FIG. 2A) therein.

Reservoir 4 is preferably a compressible tube or container. However, other types of reservoirs are contemplated such as more rigid syringe-like reservoirs. In one embodiment, as seen in FIG. 2B, reservoir 4 is compressible and configured for placement between the first and second body portions of apparatus 10 in order to be compressed as pivoting lever handle 100 is moved towards body portion. It is envisioned that reservoir 4 can be removably coupled to conduit 8a via a coupling. In this manner, reservoir 4 can be replaced as needed, such as, for example, when reservoir 4 has emptied, when a different wound closure material "W" is desired and so forth.

In use, with conduits 8 extended along or under the staple line, compression of reservoir 4 causes wound closure material "W" to be urged distally through conduit 8 and dispensed from openings 7 along the staple line and/or the knife cut line either prior to, during or after the staple firing procedure. In this embodiment, as seen in FIGS. 14-17, wound closure material "W" that is urged from openings 7 in conduits 8 is dispensed through staple slots 22c. In an alternative method of use, as actuation channel 44 is axially moved, here distally advanced, to extend conduits 8 along the staple line(s), conduits 8 are concomitantly squeezed/compressed (by actuation channel 44 passing across staple pushers 26 and/or between the walls of longitudinal slots 22a, 22b) in order to dispense wound closure material "W" therefrom. In this embodiment, compression can also be applied to reservoir 4.

Figure 5B:
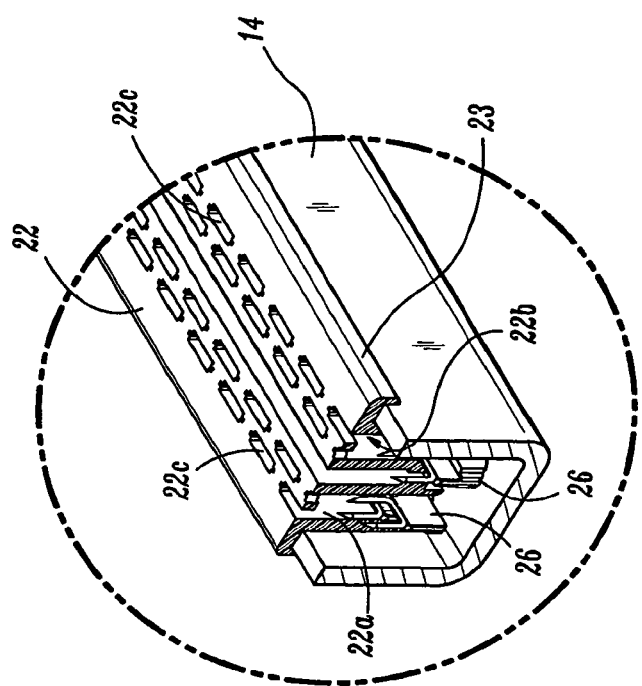
FIG. 5B is an enlarged perspective view of the indicated area in FIG. 5A showing the engagement of the cartridge lip and the retention channel.
Figure 5C:
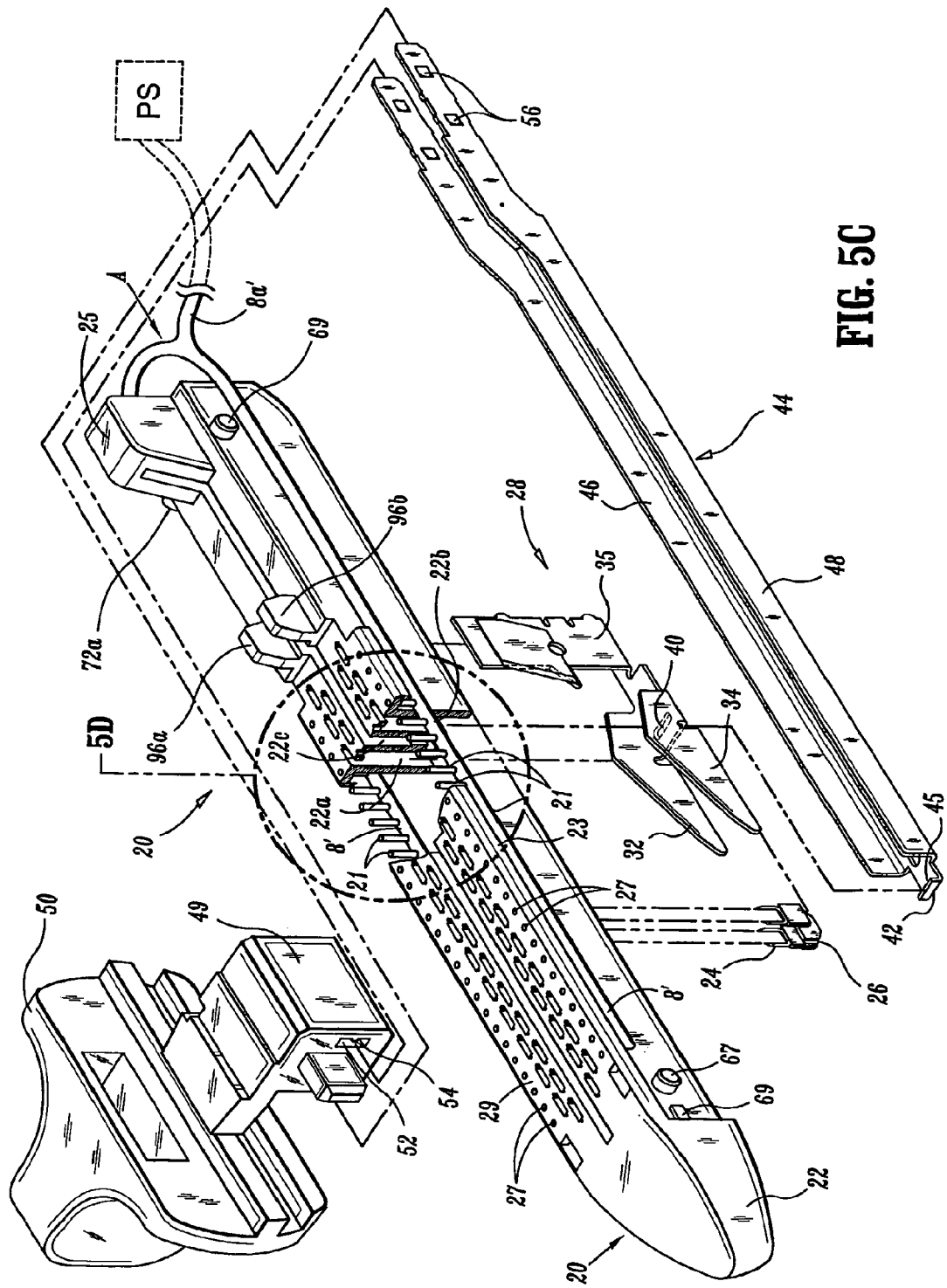
FIG. 5C is an enlarged perspective view, with parts separated, of the disposable loading unit and actuation assembly of the surgical stapling apparatus of another embodiment of the subject application.
Figure 5D:
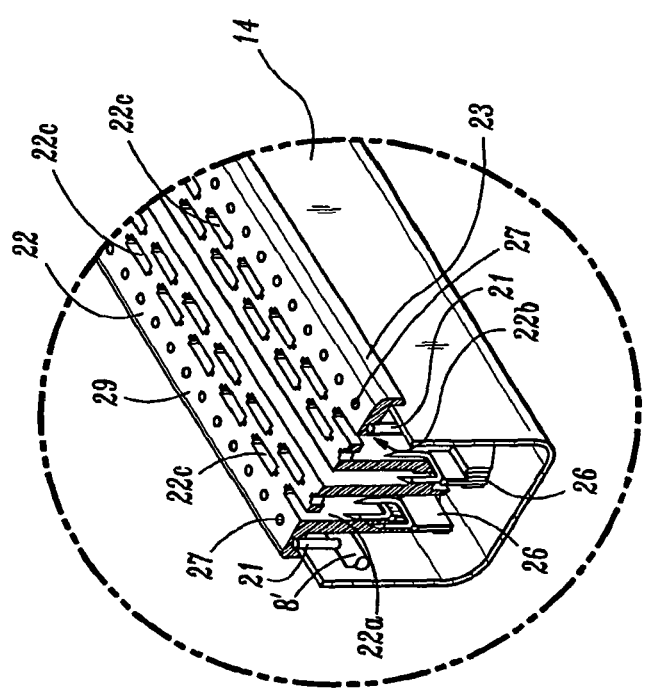
FIG. 5D is an enlarged perspective view of the indicated area in FIG. 5C showing the engagement of the cartridge lip and the retention channel.

Turning now to FIGS. 5B-5D, in an alternative embodiment, two conduits 8' extend longitudinally along opposite sides of disposable loading unit 20 of cartridge 22. Conduits 8' meet at a proximal end of cartridge 22 indicated by the letter "A" to form a main conduit 8a'. Each conduit 8' includes a plurality of micro tubes 21 (only five of each conduit 8' are shown) for feeding the at least one wound closure material "W" to or above a tissue contacting or working surface of cartridge 22 via openings 27 formed therein. Alternatively, microtubes can pass through holes placed through the outer walls of cartridge 22 and up to openings 27 in the cartridge working surface. Microtubes 21 and openings 27 can be angularly disposed to direct wound closure material toward the longitudinal center line of the working surface. Alternatively, holes can be provided in the walls defining longitudinal slots 22a, 22b to communicate with the lower portions of staple slots 22c, to feed the wound closure material through the slots.

It is envisioned that conduit 8a' is connected to a syringe or a reservoir, for example, reservoir 4 (see FIG. 2B), which stores the at least one wound closure material "W". The at least one wound closure material "W" can be manually or automatically dispensed via tubes 21 and openings 27.

For example, the at least one wound closure material "W" can be manually dispensed by directly squeezing reservoir 4 in the hand of the surgeon by indirectly squeezing reservoir 4 between lever handle 100 and cartridge half-section 11b. Alternatively, the at least one wound closure material "W" can be automatically dispensed by one or more pneumatic systems ("PS" shown in dashed lines).

It is envisioned that wound closure materials "W" include but are not limited to adhesives, hemostats and sealants. Surgical biocompatible wound closure materials which can be employed in or applied the surgical instruments, especially surgical staplers, include adhesives whose function is to attach or hold organs, tissues or structures, sealants to prevent fluid leakage, and hemostats to halt or prevent bleeding.

Examples of adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively. Examples of sealants which can be employed include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc. Examples of hemostat materials which can be employed include fibrin-based, collagen-based, oxidized regenerated cellulose-based and gelatin-based topical hemostats herein can include astringents and coagulants. Examples of commercially available hemostat materials are fibrinogen-thrombin combination materials under sold the trade designations CoStasis™ by Tyco Healthcare Group, LP and Tisseel™ sold by Baxter International, Inc. Hemostats herein include astringents, e.g., sulphates of aluminum, and coagulants.

Referring to FIGS. 2A and 4C, retention channel 14 includes a base portion 60 and two upstanding parallel walls 62 and 64. Numerical indicia are imprinted on the walls 62, 64 of retention channel 14 to indicate the length of the staple line. Retention structures in the form of notches 66a, 66b are respectively provided at the distal end of each of walls 62, 64 to engage cooperating structures in the form of protuberances 67 provided on the disposable loading unit 20. Similarly slots 68a and 68b are provided at the distal end of each of walls 62, 64 for engaging corresponding detents 69 provided on disposable loading unit 20. These structures inhibit lateral, longitudinal and perpendicular shifting of the cartridge 22 (and disposable loading unit 20) within the retaining channel 14. Ramped engagement slots 70a and 70b are also defined in the opposed walls of retention channel 14 for interacting with a pair of opposed protuberances 72a and 72b of disposable loading unit 20 (FIG. 5A) to guide disposable loading unit 20 into retention channel 14 when loaded into the surgical stapling apparatus 10.

Referring again to FIG. 2A, the surgical stapling apparatus 10 further includes an elongate anvil support beam 80 which has a generally U-shaped cross-sectional configuration. Proximal end portion 82 of support beam 80 has a notched area 84 for engaging a pair of corresponding detents 86 (only one of which is shown), which extend into the cavity 15 of body portion 12 adjacent the proximal end thereof. Detents 86 are engaged when cartridge half-section 11a and anvil half-section 11b are mated with one another. Distal end portion 88 of anvil support beam 80 is configured to support a preformed anvil plate 90 against which staples 24 are driven and formed during a stapling procedure.

Figure 10:
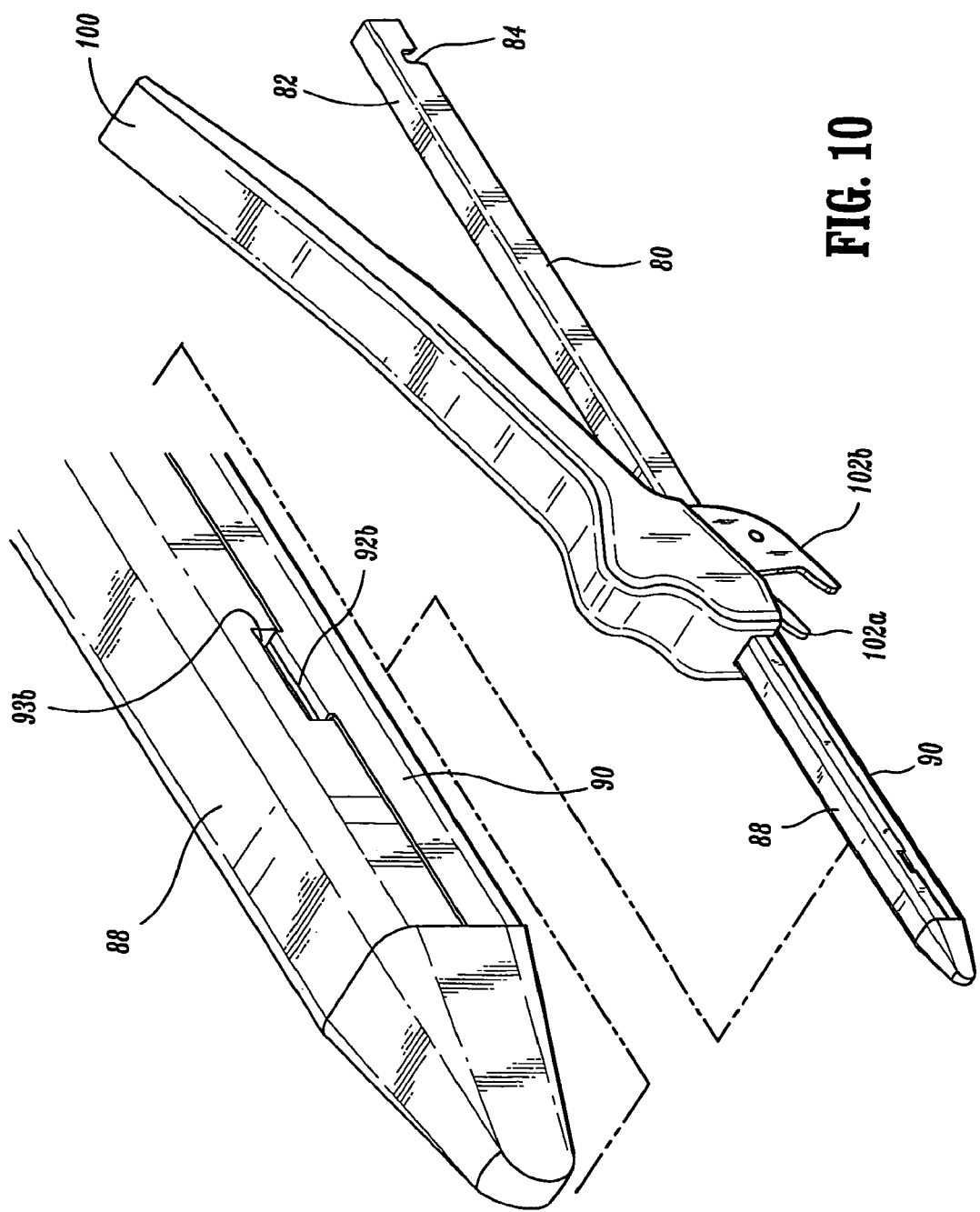
FIG. 10 is a perspective view of the anvil half-section of the surgical stapling apparatus of FIG. 1A with an enlarged localized view of a distal portion thereof illustrating the connective engagement between the anvil plate and the anvil support beam.

Referring to FIGS. 7 and 8, anvil plate 90 can be formed from a unitary piece of metal and cold formed and stamped to define a plurality of staple forming recesses or cups 91. Each staple forming recess 91 corresponds to a particular staple housed within cartridge 22. Anvil plate 90, as shown in FIG. 2A, is provided with two opposed tangs 92a and 92b which extend inwardly to engage complementary engagement slots 93b (only one is shown) in anvil support beam 80 during fabrication and assembly (see FIG. 10). The cross-sectional configuration of anvil plate 90 is dimensioned to complement the cross-sectional geometry of support beam 80 (see FIG. 9). More particularly, cavity 97 which extends along the length of anvil plate 90 corresponds to a similar channel formed in support beam 80. These areas accommodate shank 35 (see FIGS. 6A-6C) and knife blade 36 as they translate distally to form an incision in stapled body tissue during a stapling operation.

A pair of rectangular apertures 95a and 95b are formed in anvil plate 90 adjacent the proximal end thereof for receiving a pair of correspondingly positioned flanges or projections 96a and 96b which project upwardly away from the tissue contacting surface (see FIGS. 2 and 4C). The interaction between aperture 95a, 95b and flanges 96a, 96b ensures that cartridge 22 and anvil plate 90 are properly aligned with one another during a stapling procedure. Flanges 96a, 96b are spaced proximally of tissue stop portion 61 (see FIG. 3) of retention channel 14. Tissue stop portion 61 and the distal edge 13 of handle portion, best seen in FIG. 3, cooperate to prevent tissue from extending proximally.

While the above disclosure has related to a wound closure material applicator assembly operatively associated with the staple cartridge portion of stapling apparatus 10, it is envisioned and within the scope of the present disclosure that a wound closure material applicator assembly can be operatively associated with the anvil portion of stapling cartridge 10. In particular, as seen in FIGS. 9A-9F, exemplary wound closure material applicator systems are shown in/on/along anvil plate 90.

In FIG. 9A, anvil plate 90 includes a row of apertures 191 formed in each of tissue contacting or working surfaces 90a extending substantially along a length thereof. As seen in FIG. 9A, a conduit 8 extends along each row of apertures 191 and is preferably secured to the inner surface of anvil plate 90. Each conduit 8 includes a plurality of openings 7 formed therein, preferably in registration with apertures 191 formed in tissue contacting surface 90a. In this manner, wound closure material "W" can be dispensed from apertures 191 (onto tissue contacting surfaces 90a) when wound closure material "W" is urged through conduits 8.

As seen in FIG. 9B, the rows of apertures 191 can be formed in side walls 97a which define cavity 97 or knife track, and conduits 8 are affixed to the inner surface of side walls 97a in such a manner so as to place openings 7 in registration with apertures 191 formed in each of side walls 97a. In this manner, wound closure material "W" can be dispensed from apertures 191 (into cavity 97) when wound closure material "W" is urged through conduits 8.

As seen in FIG. 9C, a row of apertures 191 can be formed in a top wall 97b which defines cavity 97 and a single conduit 8 is affixed to an inner upper surface of top wall 97b in such a manner so as to place openings 7 in registration with apertures 191 formed in top wall 97b. In this manner, wound closure material "W" can be dispensed from apertures 191 (into cavity 97 or knife track) when wound closure material "W" is urged through conduit 8. Alternatively, as shown in FIG. 9D a conduit 8 with apertures 7 in its lower surface can be placed in cavity 97 and secured to the outer lower surface of top wall 97b.

As seen in FIG. 9E, a sac 192, containing wound closure material "W" therein, can be disposed in cavity 97, preferably affixed and/or secured to the walls defining cavity 97. In this manner, as knife blade 36 is distally advanced through cavity 97 of anvil 90, knife blade 36 slices or otherwise ruptures sac 192 thereby releasing/dispensing wound closure material "W" onto knife blade 36 and/or onto tissue or the knife cut line and/or the staple lines. Alternatively, as seen in FIG. 9F, a film 193 can be placed over, preferably adhered to, at least the lips defining the entrance to cavity 97 and preferably also cavity 97 and forming pockets or recesses 91. Preferably, a distal and a proximal end of a portion or all of cavity 97 is also sealed. In this manner, as knife blade 36 is distally advanced through cavity 97 of anvil 90, knife blade 36 slices through film 193 thereby releasing/dispensing wound closure material "W" onto knife blade 36 and/or tissue or the knife cut line and/or the staple lines. Moreover, as the staples (not shown) are fired into forming recesses 91, film 193 is further ruptured there to thereby dispense/release additional wound closure material "W". Film 193 can be single or multiple layers and can be comprised of wound closure material.

Alternatively, as seen in FIG. 9G, a coating of, or capsules and/or capillaries 194 containing, wound closure material "W" can be disposed in knife track or cavity 97 such that the same can be ruptured, dispensed or destroyed by knife blade 36 or some other structure, preferably moving through cavity 97, and deposited on or about tissue, the knife blade, etc. as described above.

It is envisioned that anvil plate 91 can be readily disposed of and replaced with a new anvil plate upon completion of the individual surgical step.

Referring again to FIGS. 2A and 2B, anvil half-section 11b of stapling apparatus 10 further includes clamping handle 100 which is used to securely clamp tissue between the staple forming surface of anvil plate 90 and the tissue contacting surface of cartridge 22. Clamping handle 100 is pivotably mounted to anvil support beam 80 about a transverse pivot pin which is not shown in the drawings. A pair of clamping hooks 102a and 102b depend from clamping handle 100 for interacting with U-shaped clamping beam 104 supported within the internal cavity defined in handle portion 12.

When apparatus 10 is assembled prior to use, notched area 84 at proximal end 82 of anvil support beam 80 is engaged with the cooperating detents 86 in the inner cavity 15 of body portion 12. Thereupon, anvil half-section 11b is mated with cartridge half-section 11a, and clamping handle 100 is disposed in the upright unclamped position shown in FIG. 2B. Subsequently, when body tissue is properly disposed between the staple forming surface of anvil plate 90 and the tissue contacting surface of cartridge 22, anvil half-section 11b is pivoted towards cartridge half-section 11a, about the detents in body portion 12, such that the distal ends of clamping hooks 102a and 102b are positioned immediately adjacent the proximal end of the base of U-shaped clamping beam 104. Concomitantly, flanges 96a and 96b engage apertures 95a and 95b in anvil plate 90 to ensure proper alignment of the anvil and the cartridge.

Then, to securely clamp the captured body tissue, clamping handle 100 is pivoted from the position illustrated in FIG. 1A to that which is shown in FIG. 1B. At such a time, clamping hooks 102a and 102b engage the base of clamping beam 104, locking the apparatus in a clamped condition. During clamping, the captured body tissue exerts a counter-force against the tissue contacting surface of cartridge 22 and the fastener forming surface of anvil plate 90, urging the two structures apart. To overcome these forces and prevent the proximal portion 82 of anvil support beam 80 from bending, bearing surfaces are defined within retention channel 14 to support the compressive forces generated during clamping. In particular, as illustrated in FIG. 4A, opposed bearing shelves 110a and 110b are stamp formed in opposed walls 62 and 64 of retention channel 14. The bearing shelves are positioned to abut the medial section of anvil support beam 80 proximate the clamping handle pivot point.

Figure 11:
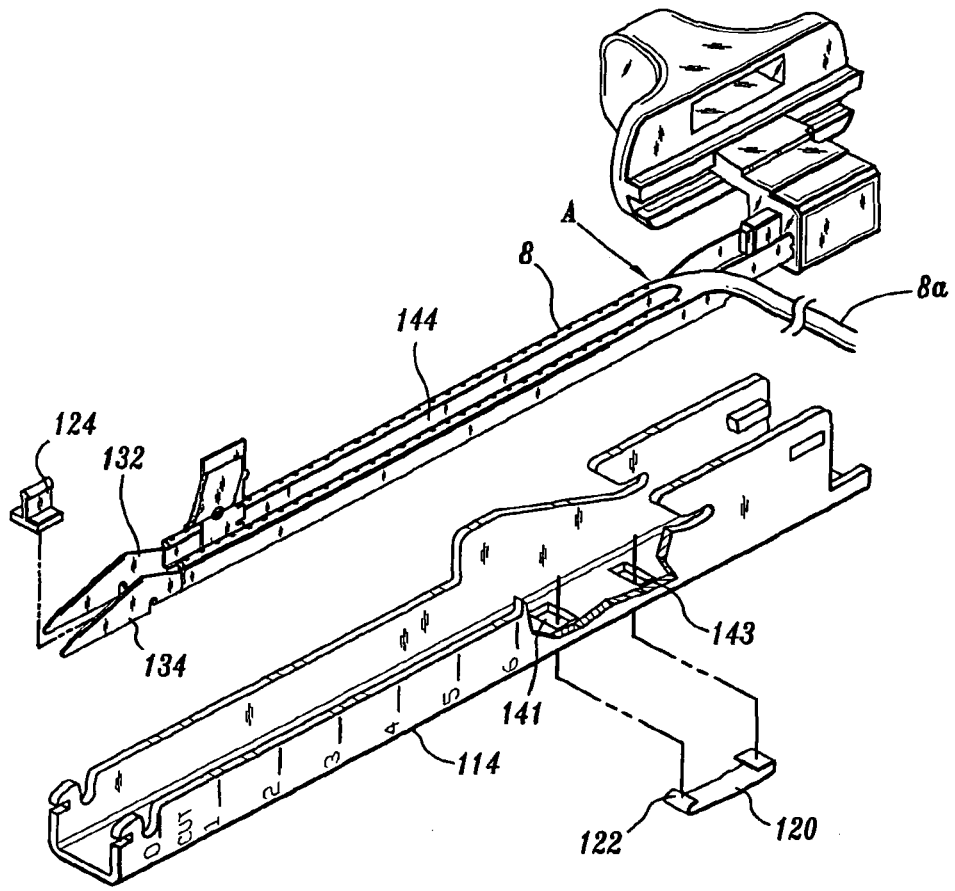
FIG. 11 is an exploded perspective view of a lockout mechanism to prevent reactuation of the apparatus.
Figure 11A:
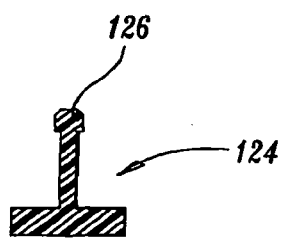
FIG. 11A is an enlarged cross-sectional view of the T-shaped member of the lockout mechanism.
Figure 12:
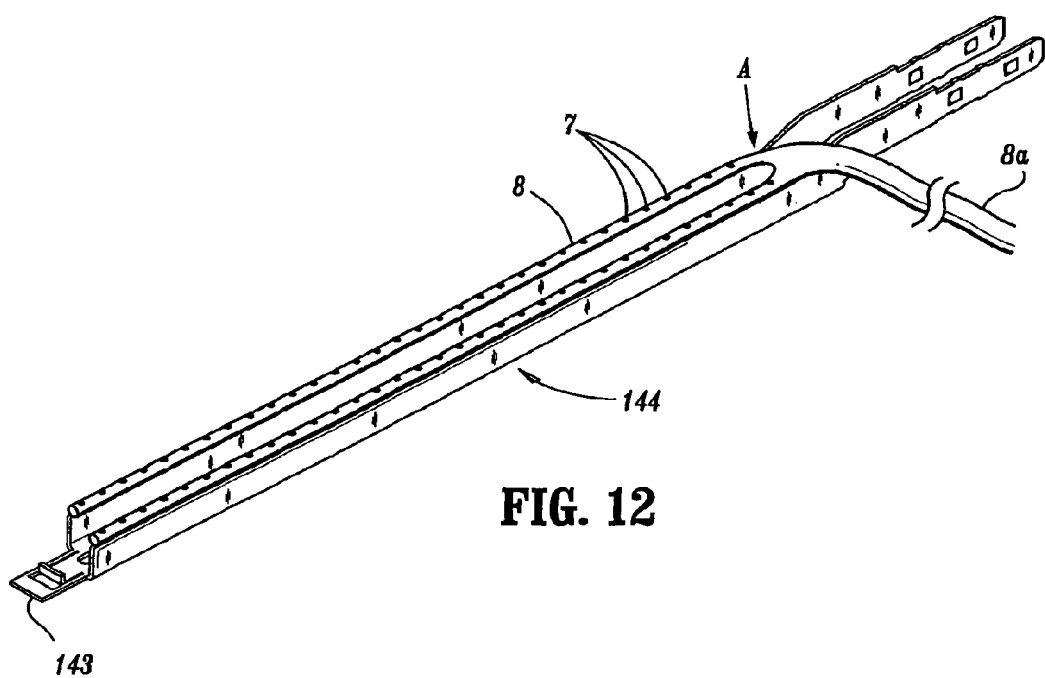
FIG. 12 is an enlarged perspective view of the actuation channel having an edge for engagement by the hook of the lockout mechanism.

It may also be desirable to provide a locking mechanism to prevent reactuation of the apparatus after it has been actuated. For example, a locking member 120 shown in FIG. 11 can be positioned in the retaining channel 114. Locking member 120 is biased to an upward engagement position and each end extends through a window 141, 143 in the channel 114. A T-shaped member 124 is positioned between the cam wedges 132, 134 to bias the hook portion 122 out of engagement with the actuation channel 144. Head portion 126 of T-shaped member 124 (FIG. 11A) is initially retained in the cartridge by a pair of detents in the cartridge which extend into the knife slot. When the apparatus is actuated, head portion 126 of T-shaped member 124 is in the knife slot.

A second pair of detents (not shown) at the distal end of the knife slot engages head portion 126 of T-shaped member 124 to hold it at the distal end of cartridge 122 when cam wedges 132, 134 are advanced to the distal position. When actuation channel 144 is retracted from the post-actuated position to the pre-actuated position, T-shaped member 124 remains forward allowing hook portion 122 to return to the upward position and extend through the window 141 in retaining channel 114 to engage edge 143 (see FIGS. 12 and 13A) of actuation channel 144 to prevent advancement of the actuation channel.

Figure 13A:
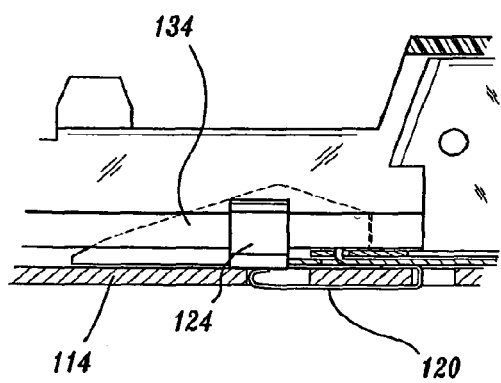
FIGS. 13A and 13B are side views of the lockout mechanism illustrating its movement from a non-engaged to an engaged position.
Figure 13B:
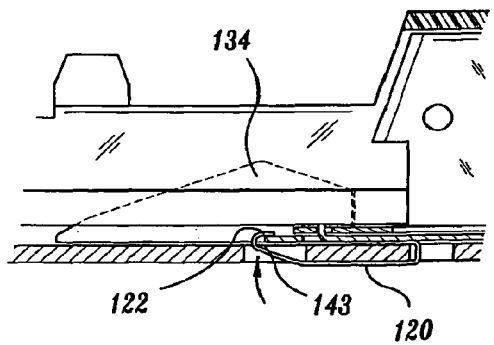

FIGS. 13A, 13B illustrate movement of the locking member 120 from an initial non-engaged position (FIG. 13A) out of engagement with actuation channel 144 to an engaged position (FIG. 13B) in engagement with actuation channel 144 to prevent distal movement thereof.

Figure 14:
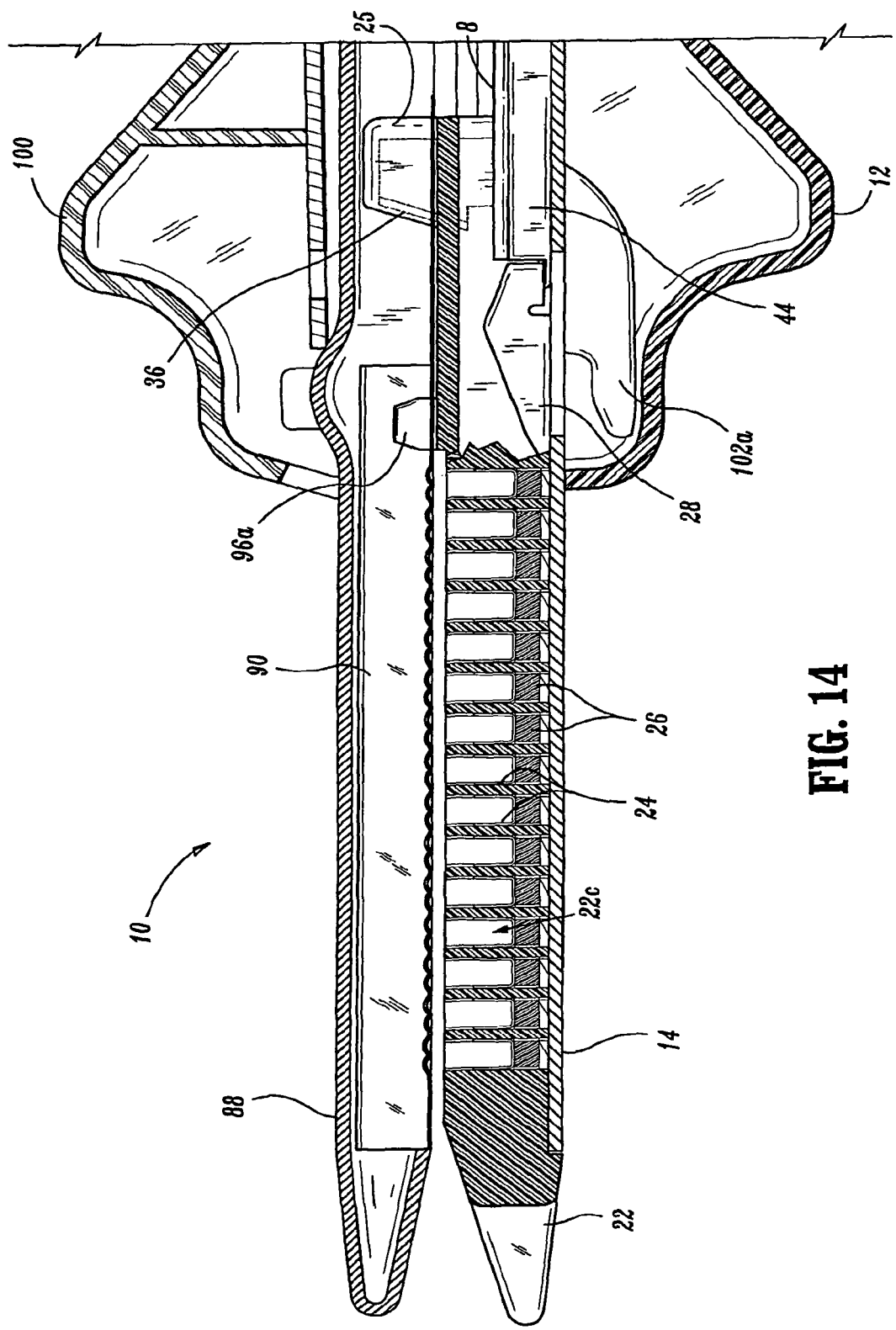
FIG. 14 is a side elevational view in cross-section of the surgical stapling apparatus of the present invention with the actuation sled disposed in a pre-actuated proximal position.
Figure 15:
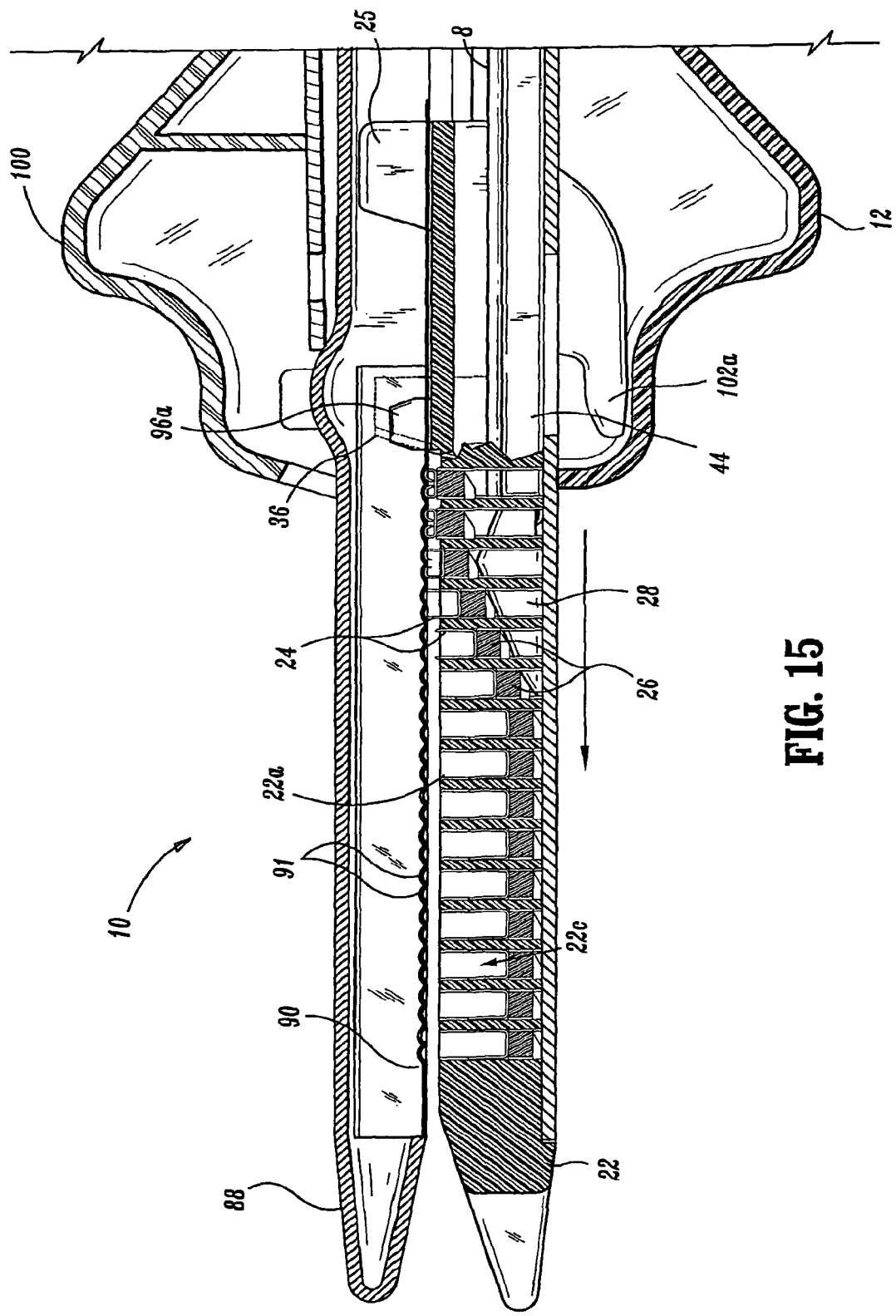
FIG. 15 is a side elevational view in cross-section of the surgical stapling apparatus of the present invention with the actuation sled disposed in a partially advanced position.

Referring now to FIGS. 14-16, there is illustrated, in sequential order, a staple firing operation in which a plurality of staples 24, preferably coated with at least one wound closure material, are ejected from cartridge 22 and driven against the staple forming surface of anvil plate 90 while knife blade 36, also preferably coated with at least one wound closure material, cuts the tissue forming a knife cut line. In operation, prior to firing surgical stapling apparatus 10, actuation sled 28 is in the proximal-most position shown in FIG. 14. At such a time, knife blade 36 is enclosed in protective housing 25 formed adjacent the proximal end of disposable loading unit 20.

To fire the apparatus, firing knob 50 (see FIG. 2A) is moved in a distal direction. Accordingly, as illustrated in FIG. 15, actuation channel 44 drives actuation sled 28 distally into and through cartridge 22. During its distal translation, the angled leading surfaces of cam wedges 32 and 34 sequentially contact ejectors 26, urging them in a direction transverse to the direction of movement of actuation sled 28. As a result, ejectors 26 push staples 24 from their individual slots 22a, driving each staple into a respective staple forming cup 91 in anvil plate 90.

Sequential firing of the staples 24 continues until actuation sled 28 is advanced to the distal end of cartridge 22, at which time, all of the staples once housed within cartridge 22 will have been ejected (see FIG. 16). Thereafter, as shown by FIG. 16, wound closure material applicator assembly 15 is actuated to dispense the at least one wound closure material "W" from openings 7 of the conduits 8 on or into the knife cut line formed by knife blade 36 and on at least one staple line to reduce, control and/or prevent bleeding along the knife cut line and the at least one staple line. It is contemplated that the wound closure material applicator assembly 15 can be actuated simultaneously with the sequential firing of the staples 24.

Firing knob 50 is then retracted to its original position, cartridge and anvil half-sections 11a, 11b are separated, and the spent disposable loading unit 20 is removed from retaining channel 14. Subsequently, a new, fully loaded disposable loading unit 20 can be positioned in retaining channel 14 such that the slot 40 of actuation sled 28 engages flange 42 of actuation channel 44 to enable re-use of the apparatus 10. Further, reservoir 4 may be replaced or refilled prior to re-use of the apparatus 10.

Another preferred embodiment of a surgical stapling apparatus according to the present disclosure will now be described with reference to FIGS. 17-19. In FIGS. 17 and 18 a surgical stapling apparatus is shown generally as 200. Fastener applying device 200 includes a housing 212 including a stationary handle 214, a distally extending body portion 216, and a transverse body portion 215. Transverse body portion 215 is configured to receive support frame 218. Housing 212 may be constructed from plastic material in the form of molded housing half-sections 212a and 212b. Housing half-sections 212a and 212b are fastened together by a plurality of screws 219. Preferably, housing 212 is constructed from fiberglass reinforced plastic, although other materials having the requisite strength requirements may be used.

A conduit 203 of a wound closure material applicator assembly 201 extends approximately the entire length of housing 212. A distal portion of conduit 203 is supported by a first leg 224 of the support frame 218. The distal portion of conduit 203 extending along or aside first leg 224 includes openings 205 for dispensing at least one wound closure material "W" therefrom to at least one staple line formed by surgical staples 221 (see FIG. 19) during or after a staple firing procedure. Conduit 203 is in fluid communication with reservoir 202 of the wound closure material applicator assembly 201 storing the at least one wound closure material. Reservoir 202 is preferably a compressible bag-like structure. However, other types of reservoirs are contemplated such as syringe-like reservoirs. Depending on the application, conduits can be flexible, semi-rigid or rigid and can include an elongate needle with an elongated bar extending through all or a portion of the needle.

Figure 19:
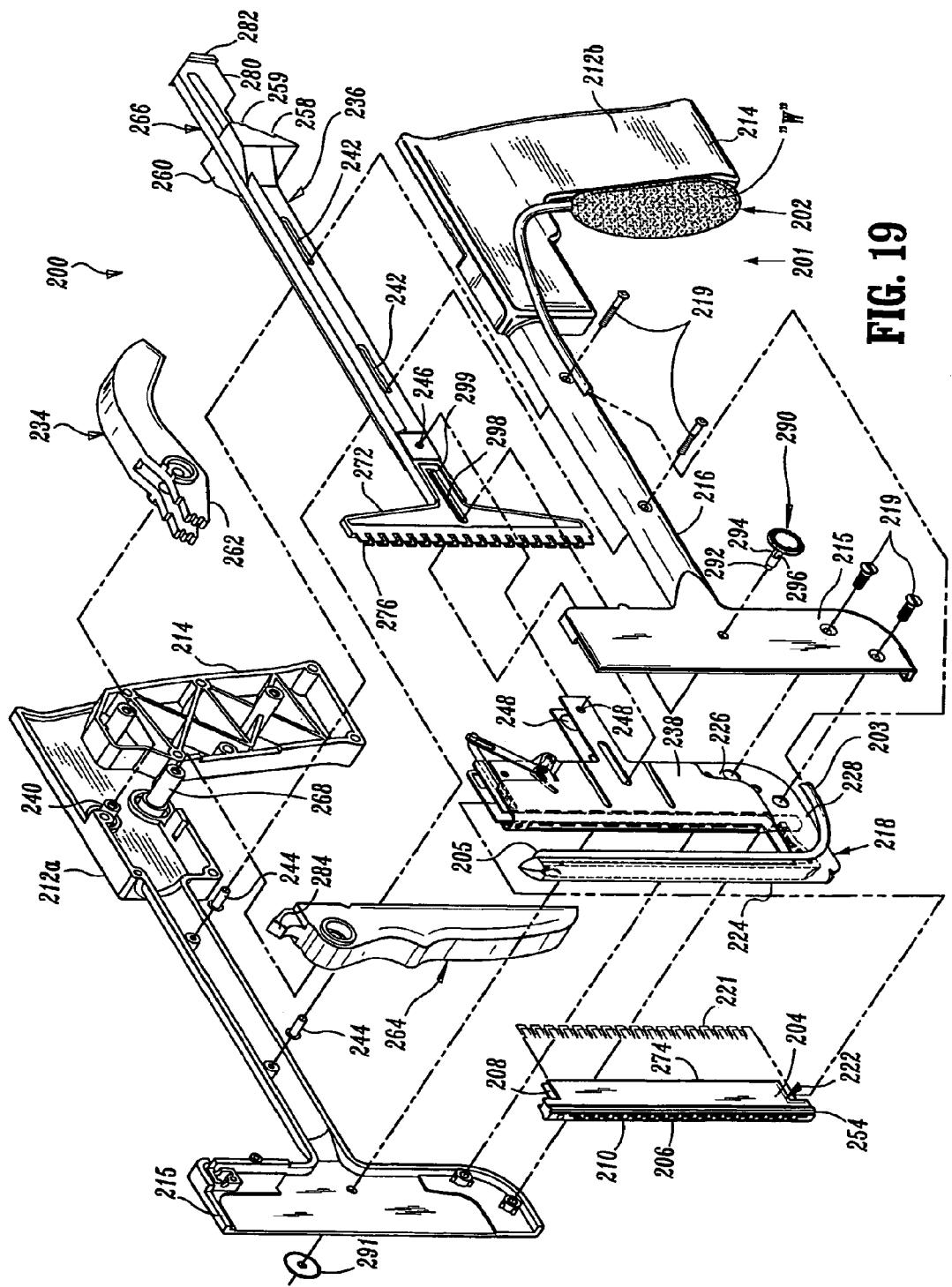
FIG. 19 is an exploded perspective view of the surgical stapling apparatus of FIG. 17.

Reservoir 202, as shown by FIGS. 17 and 19, is compressible and configured for placement between housing half-sections 212a, 212b of surgical stapling apparatus 200 for being compressed as trigger actuator 264 is moved towards stationary handle 214.

The at least one wound closure material "W" can for example be an astringent, e.g., a sulfate of aluminum, e.g., aluminum sulphate, as described herein. Surgical staples 221 are preferably also treated or coated with the or another at least one wound closure material to further facilitate hemostasis and/or another desired effect.

FIG. 19 illustrates a perspective view of surgical stapling apparatus 200 with the internal components of surgical stapling apparatus 200 separated from each other. Surgical stapling apparatus 200 may be is fastened together using screws 219 that extend between housing half-sections 212a and 212b, although adhesives, ultrasonic welding, and other known fastening methods may also be used to fasten the components of the apparatus together.

An anvil (not shown) is fastened to first leg 224 of support frame 218. Any known fastening technique may be used to fasten the anvil to first leg 224. The support frame 218 is substantially U-shaped and includes first leg 224, a second leg 226, and a base portion 228. First leg 224 extends substantially parallel to second leg 226. The support frame 218 may be monolithically formed by bending a sheet of material into the desired shape. Preferably, support frame 218 is constructed from stainless steel, although other materials having the requisite strength requirements may be used.

Cartridge carrier 238 is slidably supported about second leg 226 of support frame 218 and is movable towards first leg 224. Cartridge assembly 222 includes a body 204 having a distal face 206 which is spaced from an open proximal end 274. A pusher bar channel 208 extends from the open end 274 through a portion of body 204. A plurality of slots 210 house fasteners 221 (FIG. 19) and are configured to receive distally extending fingers 276 of pusher bar 266. The slots 210 extend between the proximal end of pusher bar channel 208 and distal face 206 of cartridge assembly 222.

Surgical stapling apparatus 200 has an approximation mechanism for advancing cartridge assembly 222 and cartridge carrier 238. An approximating clamp 234 or lever is pivotably mounted about pivot member 240 which is supported between housing half sections 212a and 212b in the proximal end of housing 212. The approximating clamp 234 is movable into engagement with a proximal end of clamp slide 236 to linearly advance clamp slide 236 within body portion 216. A plurality of longitudinal slots 242 formed in clamp slide 236 are configured to receive guide pins 244 to limit clamp slide 236 to a linear path of travel.

The distal end of clamp slide 236 includes a pair of projections 246. The projections 246 are fastened within a pair of openings 248 formed in a proximal end of cartridge carrier 238, such that linear movement of clamp slide 236 is translated to corresponding linear movement of cartridge carrier 238.

Referring to FIG. 19, approximating clamp 234 includes an abutment end 262 having a series of detents which are configured to be received in recesses 258 and 259 formed in an angled proximal end 260 of clamp slide 236. Angled proximal end 260 of clamp slide 236 and abutment end 262 of approximating clamp 234 are movable into engagement to advance cartridge assembly 222 towards the anvil on the first leg 224. Preferably, approximating clamp 234 is constructed of plastic and clamp slide 236, cartridge carrier 238 and pusher bar 266 are constructed of stainless steel.

FIG. 19 illustrates the firing mechanism for applying the fasteners of apparatus 200. The firing mechanism includes trigger actuator 264 and elongate pusher bar 266 slidably received in a channel formed in clamp slide 236. Trigger actuator 264 is pivotable about pivot pin 268 into engagement with a proximal end of pusher bar 266 to advance pusher bar 266 with respect to cartridge carrier 238 and to compress reservoir 202. Pivot pin 268 is supported between housing half-sections 212a and 212b.

The slots 242 of pusher bar 266 slidably receive the guide pins 244. Guide pins 244 limit pusher bar 266 to a linear path of travel identical to that of clamp slide 236. The distal end of pusher bar 266 is formed with a head portion 272 configured to move through the open proximal end 274 of cartridge assembly 222 to effect ejection of fasteners 221. The plurality of distally extending fingers 276 are integrally formed on head portion 272. Each finger 276 has a concave distal surface configured to engage fasteners 221 housed within cartridge assembly 222 and engage the fasteners 221. Fingers 276 extend from head portion 272 in a pattern that corresponds to the pattern that fasteners 221 are housed within cartridge assembly 222. For example, the pattern may be two staggered rows. Other patterns are also contemplated.

As illustrated in FIG. 19, the proximal end of pusher bar 266 has a locking surface 280 and a contact surface 282. The trigger actuator 264 includes an engagement surface 284 which pivots into engagement with contact surface 282 of the pusher bar 266 to distally advance pusher bar 266 when trigger actuator 264 is squeezed.

When pusher bar 266 is in a retracted position, locking surface 280 of pusher bar 266 is positioned to prevent engagement between engagement surface 284 of trigger actuator 264 and contact surface 282 of pusher bar 266. Thus, locking surface 280 prevents firing fasteners 221 prior to sufficient approximation of cartridge assembly 222 and the anvil. Before trigger actuator 264 can be rotated counter-clockwise to eject fasteners 221 from device 200, approximating clamp 234 must be rotated toward stationary handle 214 to advance clamp slide 236 distally. This frees trigger actuator 264 for pivotal movement to fire cartridge assembly 222 and eject fasteners 221.

An adjustment member 290 is provided in the distal end of apparatus 200 to facilitate ejection of fasteners 221 from apparatus 200. Adjustment member 290 includes a cylindrical shaft 292 having a pair of diametrically opposed first and second flats 294 and 296, respectively. Cylindrical shaft 292 extends through an opening formed in second leg 226 of support member 218 and through the distal end of a longitudinal adjustment slot 298 formed in pusher bar 266. Adjustment member 290 is secured to support member 218 by adjustment nut 291. Shaft 292 is rotatable to align one of opposed flats 294 or 296 with a proximal end 299 of adjustment slot 298 to define a stop surface for pusher bar 266. Since flats 294 and 296 are formed at different depths into cylindrical shaft 292, shaft 292 may be rotated to change the position of the stop surface to vary the stroke of pusher bar 266.

It is envisioned that, prior, during or after firing of cartridge assembly 222 to eject fasteners 221, wound closure material applicator assembly 201 is actuated to dispense the at least one wound closure material "W" from openings 205 of conduit 203 to the at least one staple line defined by fasteners 21 and/or the knife cut line if there is one to control and/or prevent bleeding along the knife cut line or at least one staple line.

An alignment mechanism is operatively connected to the approximation mechanism to maintain alignment between cartridge assembly 222 and the anvil during approximation of the anvil and cartridge assembly 222. A more detailed description of a surgical stapling apparatus similar to apparatus 200 is found in commonly assigned U.S. Pat. No. 5,964,394, the entire contents of which are incorporated herein by reference.

Figure 20:
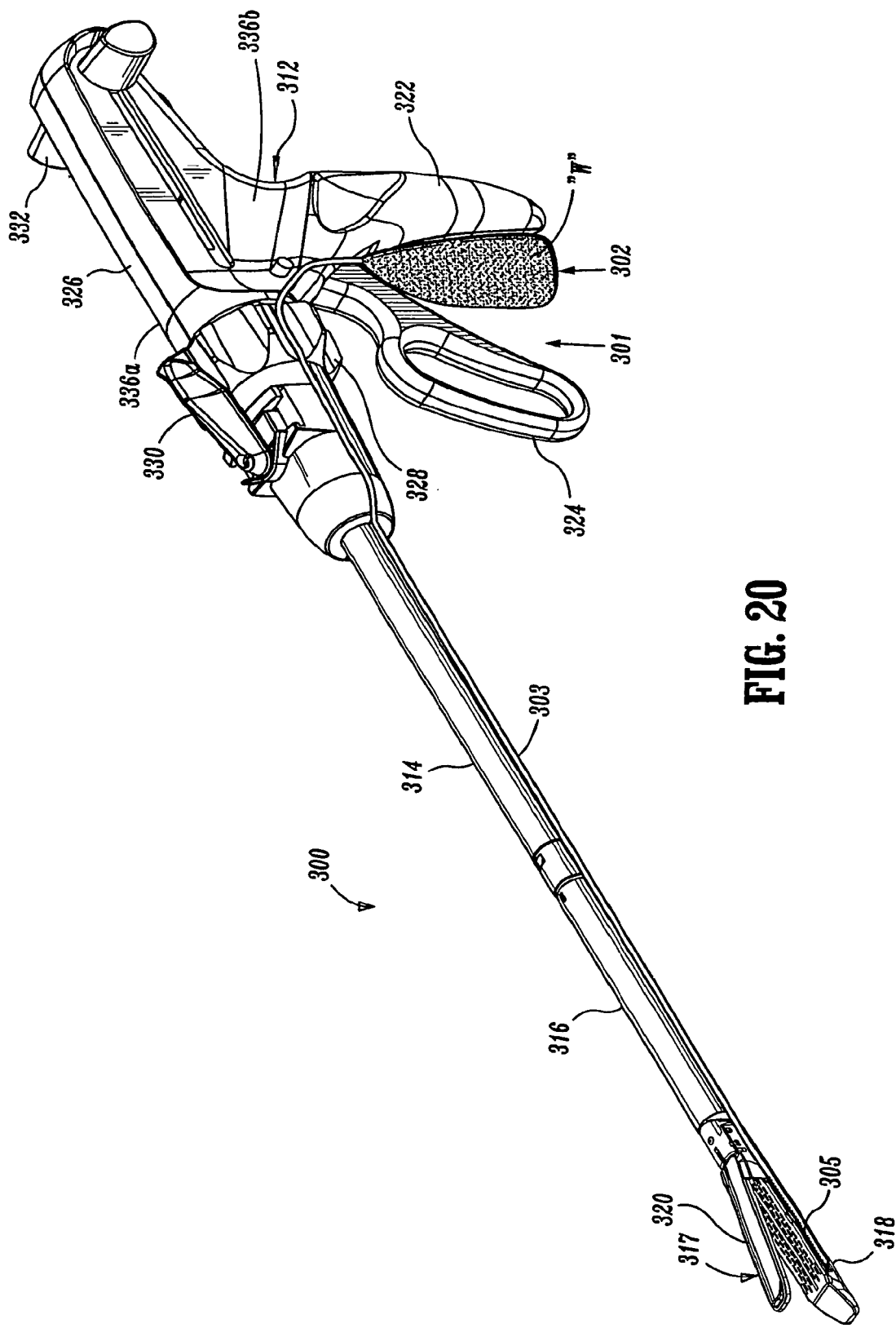
FIG. 20 is a perspective view of yet another surgical stapling apparatus having a wound closure material applicator assembly operatively associated therewith.
Figure 21:
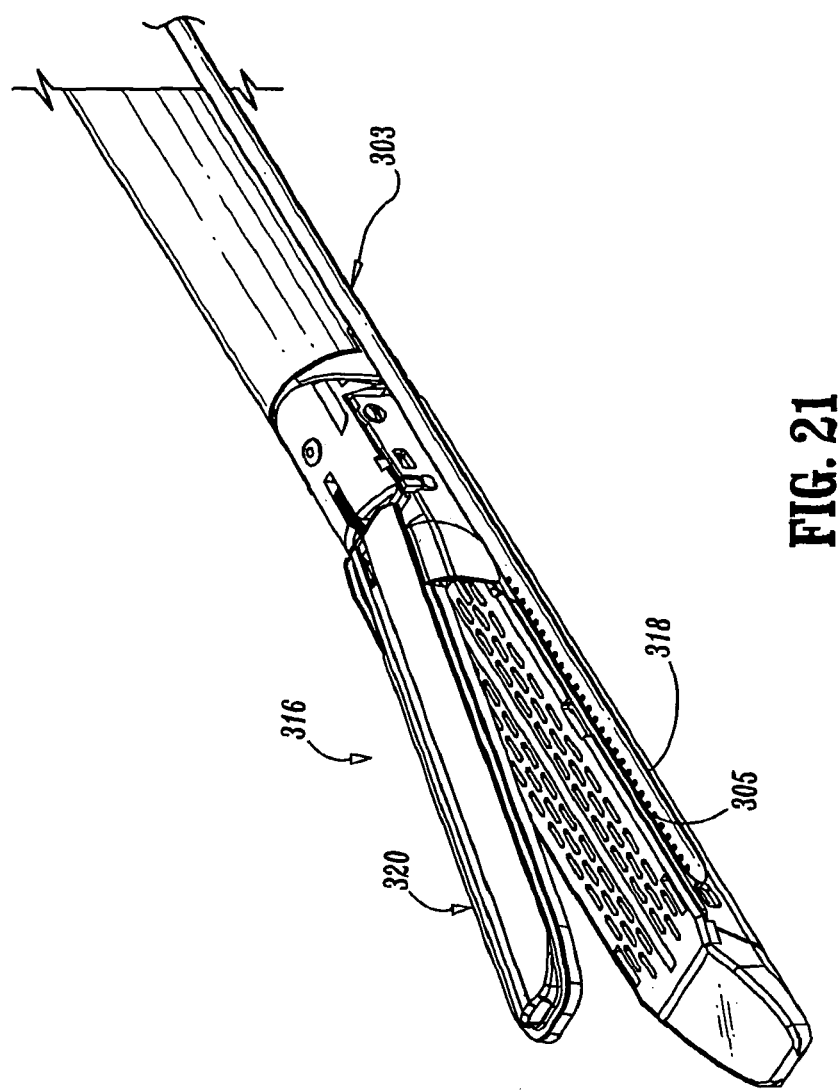
FIG. 21 is a perspective view of a distal end of the surgical stapling apparatus of FIG. 20.

With reference to FIGS. 20 and 21, another preferred embodiment of a surgical stapling apparatus according to the present disclosure is shown generally as 300. Surgical stapling apparatus 300 includes a handle assembly 312 and an elongated body 314 extending from handle assembly 312. A disposable loading unit or DLU 316 is releasably secured to a distal end of elongated body 314. DLU 316 includes a tool assembly or end effecter 317 having a cartridge assembly 318 housing a plurality of metallic surgical staples (not shown) and an anvil assembly 320 movably secured in relation to cartridge assembly 318.

The staples are preferably treated or coated with at least one wound closure material "W" as shown in FIG. 16A above.

Handle assembly 312 includes a stationary handle member 322, a movable handle member 324, and a barrel portion 326. Handle assembly 312 includes housing 336, which is preferably formed from molded housing half-sections 336a and 336b, which forms stationary handle member 322 and barrel portion 326 of handle assembly 312. Movable handle member 324 is pivotably supported between housing half-sections 336a and 336b.

A conduit 303 of a wound closure material applicator assembly 301 extends along a portion of handle assembly 312, along the entire length of elongate body 314 and DLU 316, and at least a portion of the entire length of cartridge assembly 318 or anvil assembly 320 (here shown on cartridge assembly 318). As seen in FIG. 21, a distal portion of conduit 303 includes openings 305 for dispensing at least one wound closure material "W" therefrom on at least one staple line formed by the staples and/or on the knife cut line during a staple firing procedure. Openings 305 preferably are directed toward or in the direction of the tissue to be treated desirably in the area when the tissue has been perforated or cut.

Conduit 303 is in fluid communication with a reservoir 302 of the wound closure material applicator assembly 301 which stores the at least one wound closure material "W". Reservoir 302 is preferably a compressible tube, bag, sac or capsule. However, other types of reservoirs are contemplated such as syringe-like reservoirs. A portion of conduit 303 in communication with or couplable with a reservoir or source of wound closure material can be provided in fluid couplable sections. For example, a DLU can have a portion of conduit 303 which can be joined or fluidly couplable with another portion of conduit that is provided on the handle or shaft portion of the stapling instrument.

Reservoir 302, as shown by FIG. 20, is compressible and configured for placement between housing half-section 336a, 336b of apparatus 300 for being compressed as movable handle member 324 is moved towards stationary handle member 322. Accordingly, compression of reservoir 302 causes wound closure material "W" to be urged through conduit 303 and dispensed from openings 305 along the staple line either prior to, during or after the staple firing procedure.

A rotatable member 328 is preferably mounted on the forward end of barrel portion 326 to facilitate rotation of elongated body 314 with respect to handle assembly 312. An articulation lever 330 is also preferably mounted on the forward end of barrel portion 326 adjacent rotatable knob 328 to facilitate articulation of tool assembly 317. A pair of retraction knobs 332 are movably positioned along barrel portion 326 to return surgical stapling apparatus 300 to a retracted position. A more detailed description of a surgical stapling apparatus similar to apparatus 300 is described in U.S. Pat. No. 6,330,965, the entire contents of which are incorporated herein by reference.

It is provided that other types of staplers from those described herein, for example, circular staplers, can be designed to include a wound closure material applicator assembly for providing at least one wound closure material along a knife cut line and/or at least one staple line before, during and/or after a stapling procedure to facilitate desirable effects to the stapled and/or cut tissue.

It is provided that a number of different wound closure materials "W" can be individually dispensed, or a combination of the number of different wound closure materials "W" can be dispensed by the wound closure material applicator assemblies disclosed herein.

It is envisioned that the openings (i.e., openings 7, 205 and 305) and microtubes 21, disclosed in the embodiments above, are closed or are sealed/covered over with a material having a region of reduced weakness, to thereby enable rupturing of the region of reduced weakness upon urging of fluid (e.g., wound closure material "W") through the conduits.

Alternatively, it is envisioned that a seal (not shown) is provided in the lumen of each conduit 8, preferably at a location proximal of the openings formed therein or of the microtubes extending therefrom. The seal maintains wound closure material "W" from prematurely entering the conduits and seeping out of the openings formed therein. Accordingly, when wound closure material "W" is urged through conduits 8, the fluid pressure ruptures the seal and wound closure material "W" enters into conduits 8. It is further contemplated that a valve "V" (see FIGS. 1a-2B) can be provided along the length of conduit 8 or 8a at a location proximal of the openings formed therein or of the microtubes.

Although the subject apparatus has been described with respect to preferred embodiments, it will be readily apparent, to those having ordinary skill in the art to which it appertains, that changes and modifications may be made thereto without departing from the spirit or scope of the subject apparatus.

What is claimed is:

1. A surgical stapling apparatus for joining tissue, the surgical stapling apparatus comprising:
    a handle assembly including a stationary handle member and a movable handle member pivotally associated with the stationary handle member;
    an elongated body extending distally from the handle assembly;
    a stapling assembly secured to a distal end of the elongated body, the stapling assembly including a cartridge assembly and an anvil assembly moveably secured to the cartridge assembly; and
    a wound closure material applicator assembly including:
        a compressible reservoir disposed between the moveable handle member and the stationary handle member;
        a wound closure material contained in the compressible reservoir; and
        a conduit in fluid communication with the compressible reservoir, the conduit extending along the elongated body, the conduit including a distal portion extending along at least part of a length of at least one of the cartridge assembly and the anvil assembly, the distal portion of the conduit having a plurality of openings.

2. The surgical stapling apparatus of claim 1, wherein the handle assembly includes an unactuated position and an actuated position, and the compressible reservoir includes an uncompressed state and a compressed state, in the unactuated position the movable handle member is separated from the stationary handle member and as the handle assembly transitions to the actuated position the moveable handle member is moved towards the stationary handle member, in the uncompressed state the compressible reservoir is substantially uncompressed and in the compressed state the compressible reservoir is at least partially compressed between the moveable handle member and the stationary handle member as the handle assembly transitions from the unactuated to the actuated position, the at least partial compression of the compressible reservoir dispensing the wound closure material from the plurality of openings of the distal portion of the conduit.

3. The surgical stapling apparatus of claim 1, wherein the cartridge assembly and the anvil assembly each have a tissue contacting surface, and wherein the plurality of openings of the distal portion of the conduit are directed towards the tissue contacting surfaces.

4. The surgical stapling apparatus of claim 1, wherein the conduit is removably secured to an exterior surface of the elongated body.

5. The surgical stapling apparatus of claim 1, wherein the distal portion of the conduit is removably secured to an exterior surface of at least one of the cartridge assembly and the anvil assembly.

6. The surgical stapling apparatus of claim 1, wherein the distal portion of the conduit is disposed within at least one of cartridge assembly and the anvil assembly.

7. The surgical stapling apparatus of claim 1, wherein the distal portion includes a first conduit branch and a second conduit branch, each conduit branch having a plurality of openings; and wherein each branch is in fluid communication with the reservoir.

8. The surgical stapling apparatus of claim 1, wherein the compressible reservoir is selectively fluidly coupled to the conduit and removably secured between the moveable handle member and the stationary handle member.

9. The surgical stapling apparatus of claim 1, wherein the wound closure material is at least one of an adhesive, a hemostat, a coagulant, an astringent, and a sealant.

10. The surgical stapling apparatus of claim 1, wherein the wound closure material is selected from the group consisting of: aldehyde-based adhesive materials, albumin/glutaraldehyde materials, cyanoacrylate-based materials, fibrin sealants, and collagen-based sealants, synthetic polymer-based sealants, synthetic polyethylene glycol based hydrogel materials, fibrin-based hemostats, collagen-based hemostats, oxidized regenerated cellulose-based hemostats, gelatin-based hemostats, fibrinogen-thrombin combination materials, and sulphates of aluminum.

11. A method of joining tissue comprising the steps of:
providing a surgical stapling apparatus including:
a handle assembly having a stationary handle member and a movable handle member pivotally associated with the stationary handle member;
an elongated body extending distally from the handle assembly; and
a stapling assembly secured to a distal end of the elongated body, the stapling assembly including an anvil assembly moveably secured to a cartridge assembly, the cartridge assembly having a plurality of staples disposed within staple slots, and the stapling assembly including a driving member for firing the staples from the staple slots and against the anvil assembly;
providing a wound closure material applicator assembly including:
a compressible reservoir;
a wound closure material contained in the compressible reservoir; and
a conduit having a distal portion with a plurality of openings;
placing the compressible reservoir between the moveable handle member and the stationary handle member, the compressible reservoir being in fluid communication with the conduit;
dispensing the wound closure material from at least one of the plurality of openings by approximating the movable handle member and the stationary handle member such that the compressible reservoir is at least partially compressed; and
firing the staple assembly.

12. The method of claim 11, wherein the step of firing includes moving the movable handle member towards the stationary handle member beyond a firing position before, during, or after the step of dispensing the wound closure material.

13. The method of claim 11, wherein the step of placing the compressible reservoir includes securing the conduit to the elongated body and securing the distal portion of the conduit to at least one of the cartridge assembly and the anvil assembly.

14. The method of claim 13, wherein the step of securing the distal portion includes directing the openings towards a tissue contacting surface of at least one of the cartridge assembly and the anvil assembly.

15. The method of claim 11, wherein the step of placing the compressible reservoir includes coupling the conduit to the compressible reservoir.

16. The method of claim 15, wherein the distal portion of the conduit is within at least one of the cartridge assembly and the anvil assembly.

17. A method of joining tissue comprising the steps of:
providing a surgical apparatus for joining tissue including:
a handle assembly including a stationary portion and a movable handle member pivotally associated with the stationary portion;
an elongated body extending distally from the handle assembly; and
a tissue joining assembly secured to a distal end of the elongated body including a first jaw moveably secured to a second jaw, wherein the tissue joining assembly is capable of firing a plurality of staples when the movable handle member moves past a fire position;
providing a wound closure material applicator assembly including a wound closure material contained in a compressible reservoir and a conduit having a distal portion with a plurality of openings in fluid communication with the compressible reservoir;
placing the compressible reservoir between the moveable handle member and the stationary portion;
dispensing the wound closure material from at least one of the plurality of openings by approximating the movable handle member and the stationary portion such that the compressible reservoir is at least partially compressed; and
firing the plurality of staples from the tissue joining assembly.

18. The method of claim 17, wherein the step of placing the compressible reservoir includes securing the conduit to the elongated body and securing the distal portion of the conduit to at least one of the first jaw and the second jaw.

19. The method of claim 17, wherein the step of placing the compressible reservoir includes coupling the conduit to the compressible reservoir.

20. The method of claim 17, wherein the step of firing occurs before, during, or after the step of dispensing the wound closure material.

* * * * *